(12) United States Patent
McGurk et al.

(10) Patent No.: US 11,911,048 B2
(45) Date of Patent: Feb. 27, 2024

(54) VARIABLE ANGLE DRILL GUIDE

(71) Applicant: DEPUY SYNTHES PRODUCTS, INC., Raynham, MA (US)

(72) Inventors: Michael McGurk, Williamstown, NJ (US); Henri Défossez, Neuchatel (CH); Simon Wampfler, Utzenstorf (CH); Gregor Spreiter, Bern (CH); Frederic Gueissaz, Reconvilier (CH); Marcel Schweizer, Liebefeld (CH); Said Ghammar, Zuchwil (CH); Andreas Baeriswyl, Büren an der Aare (CH); Mirko Rocci, Bettlach (CH); Steffan Daniel, Solothurn (CH)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 68 days.

(21) Appl. No.: 17/541,676

(22) Filed: Dec. 3, 2021

(65) Prior Publication Data
US 2023/0172621 A1 Jun. 8, 2023

(51) Int. Cl.
*A61B 17/17* (2006.01)
*A61B 17/00* (2006.01)
*A61B 90/00* (2016.01)

(52) U.S. Cl.
CPC .. *A61B 17/1728* (2013.01); *A61B 2017/0046* (2013.01); *A61B 2017/00862* (2013.01); *A61B 2090/034* (2016.02)

(58) Field of Classification Search
CPC ............ A61B 17/1728; A61B 17/1775; A61B 17/1782; A61B 17/8872; A61B 2090/034; A61B 2017/0046; A61B 2017/00862; B25G 3/10
See application file for complete search history.

(56) References Cited

U.S. PATENT DOCUMENTS

| | | | |
|---|---|---|---|
| 7,883,513 B2 | 2/2011 | Ralph et al. | |
| 9,402,663 B2* | 8/2016 | Peterson | A61B 50/33 |
| 2009/0204157 A1 | 8/2009 | Fernandez Dell'Oca | |
| 2010/0130983 A1 | 5/2010 | Thurnhill | |
| 2010/0294087 A1* | 11/2010 | Hu | B25B 23/108 |
| | | | 81/125 |
| 2013/0012945 A1 | 1/2013 | Chreene et al. | |
| 2018/0353301 A1 | 12/2018 | Goldstein et al. | |
| 2019/0275649 A1* | 9/2019 | Nakagawa | B25B 23/108 |
| 2021/0177471 A1* | 6/2021 | Detweiler | A61B 17/808 |

* cited by examiner

*Primary Examiner* — Tracy L Kamikawa
(74) *Attorney, Agent, or Firm* — Kramer & Amado, P.C.

(57) ABSTRACT

A drill guide handle configured to engage a variable angle drill guide, including: a handle grip; a first cannula extending from a proximal end of the drill guide handle to a distal end of the drill guide handle, wherein the first cannula is configured to provide a zero degree insertion angle for a drill bit; and a body including: a first tab and a second tab wherein the first and second tabs include a first and second tab protrusion, respectively, wherein each of the first tab and the second is configured to flex so that the first and second tab protrusions engage a horizontal groove on a variable angle drill guide; and a body protrusion on an inner surface of the body, wherein the body protrusion is configured to engage a vertical grove on the variable angle drill guide.

16 Claims, 14 Drawing Sheets

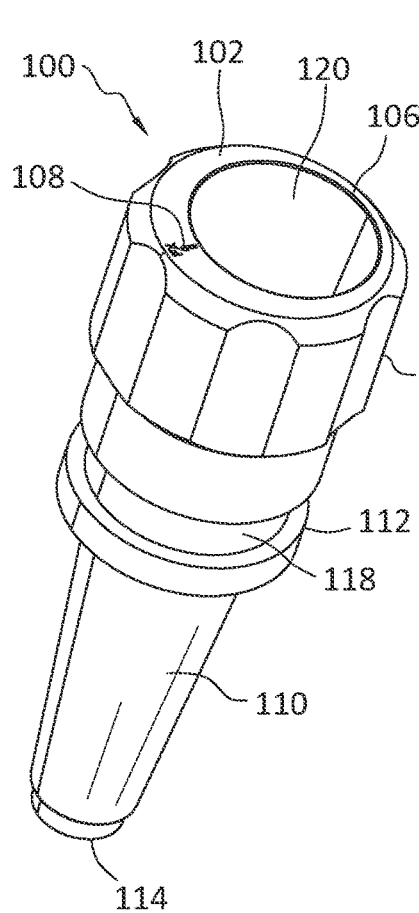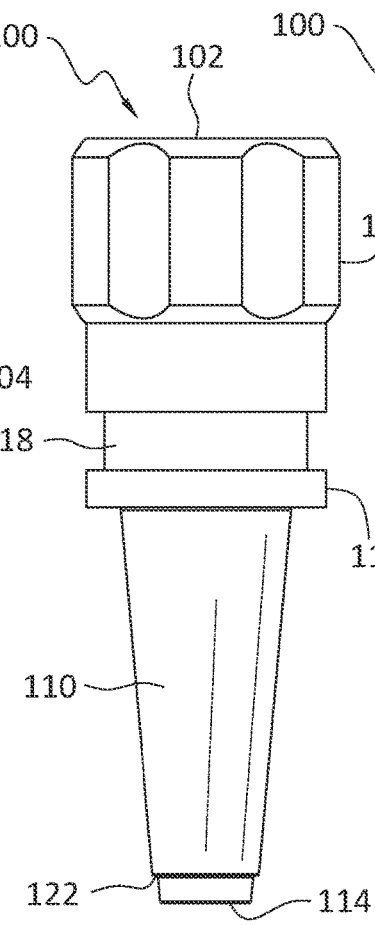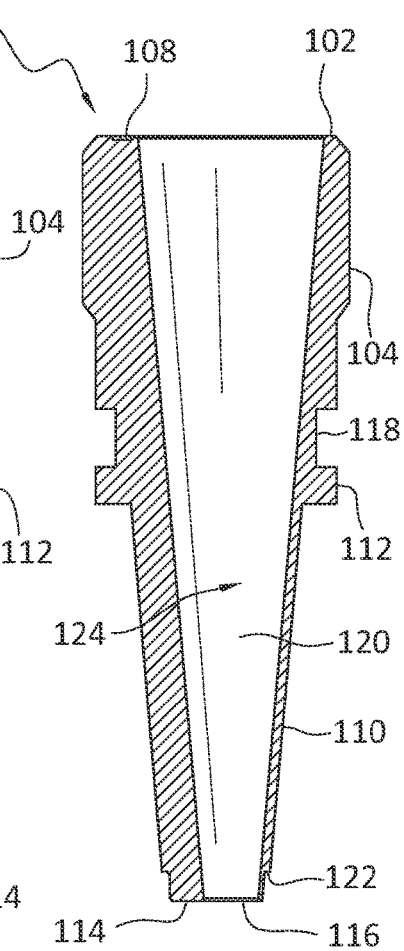
FIG. 1A    FIG. 1B    FIG. 1C
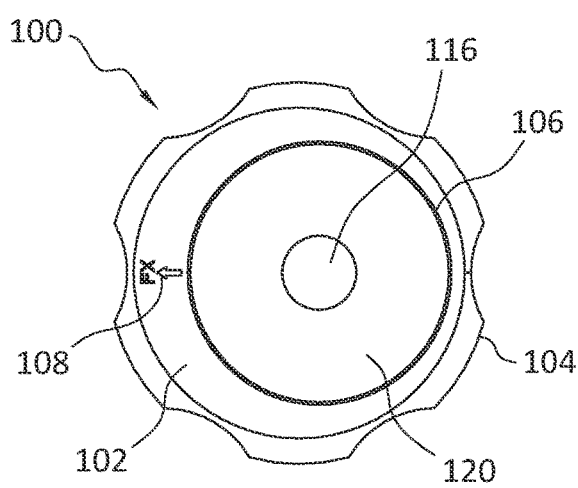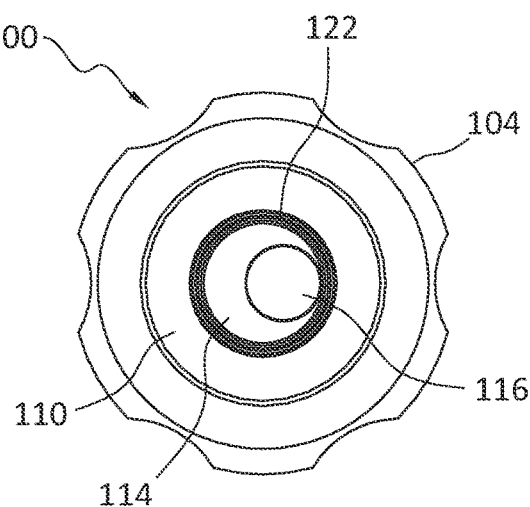
FIG. 1D    FIG. 1E

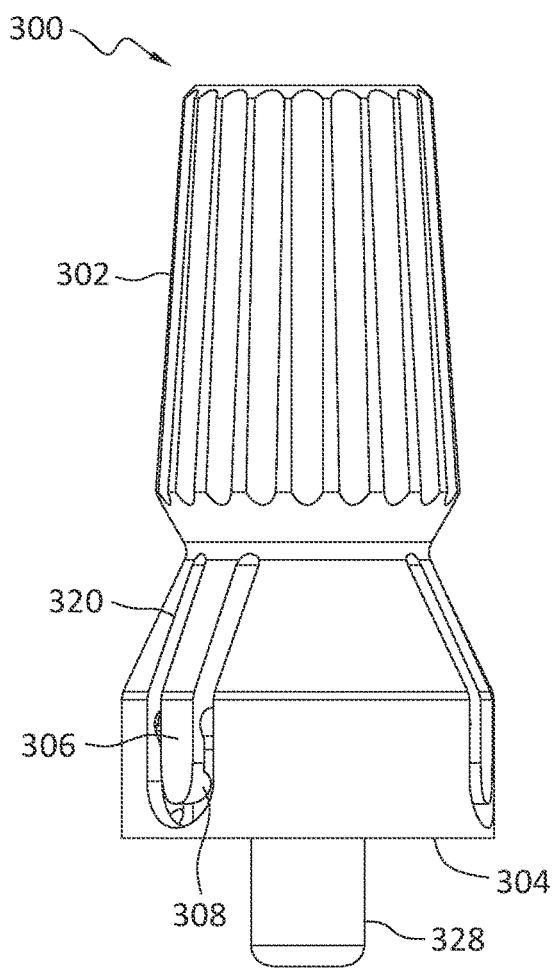
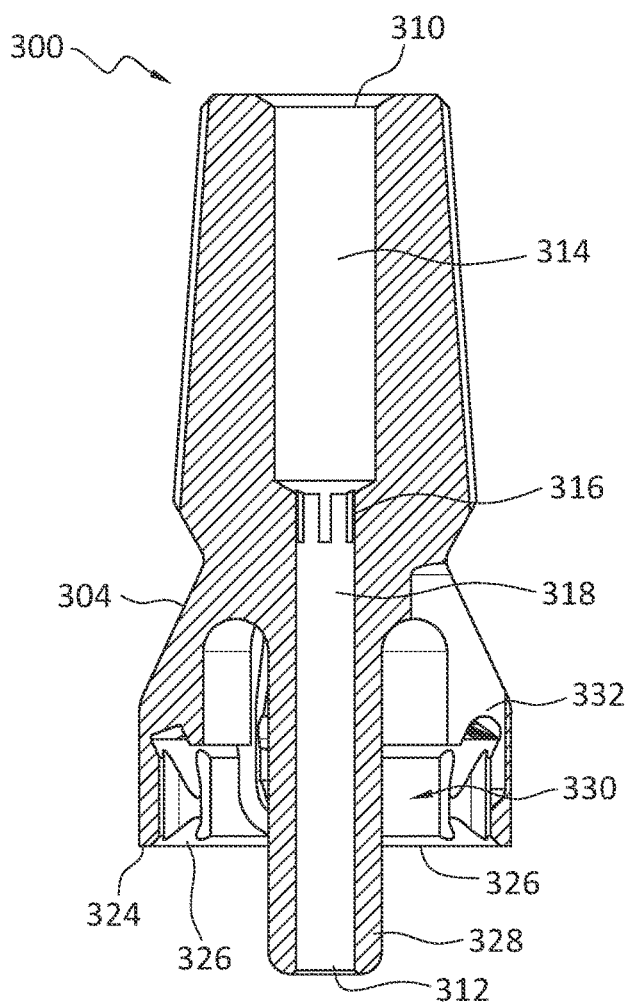
FIG. 7C
FIG. 7D
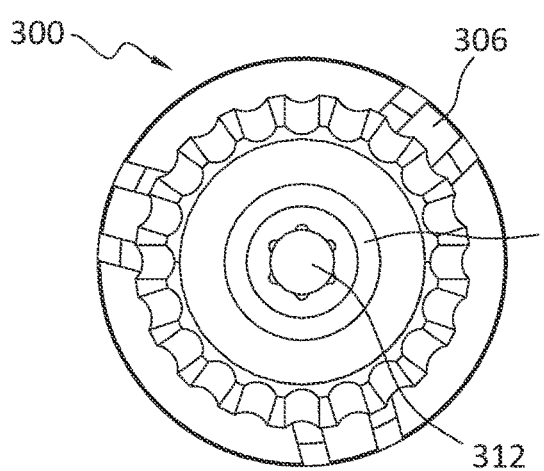
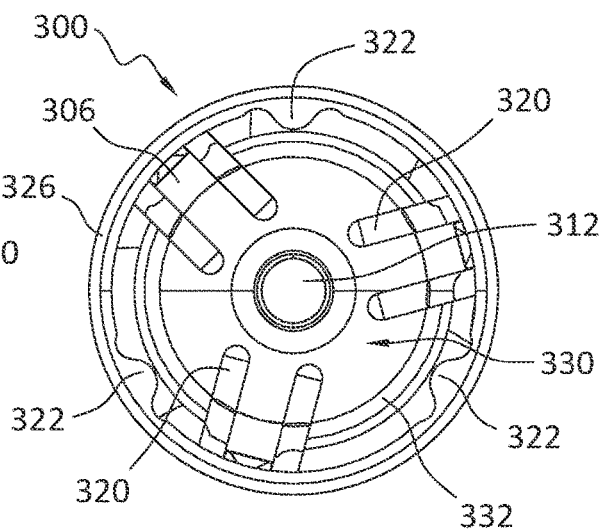
FIG. 7E
FIG. 7F

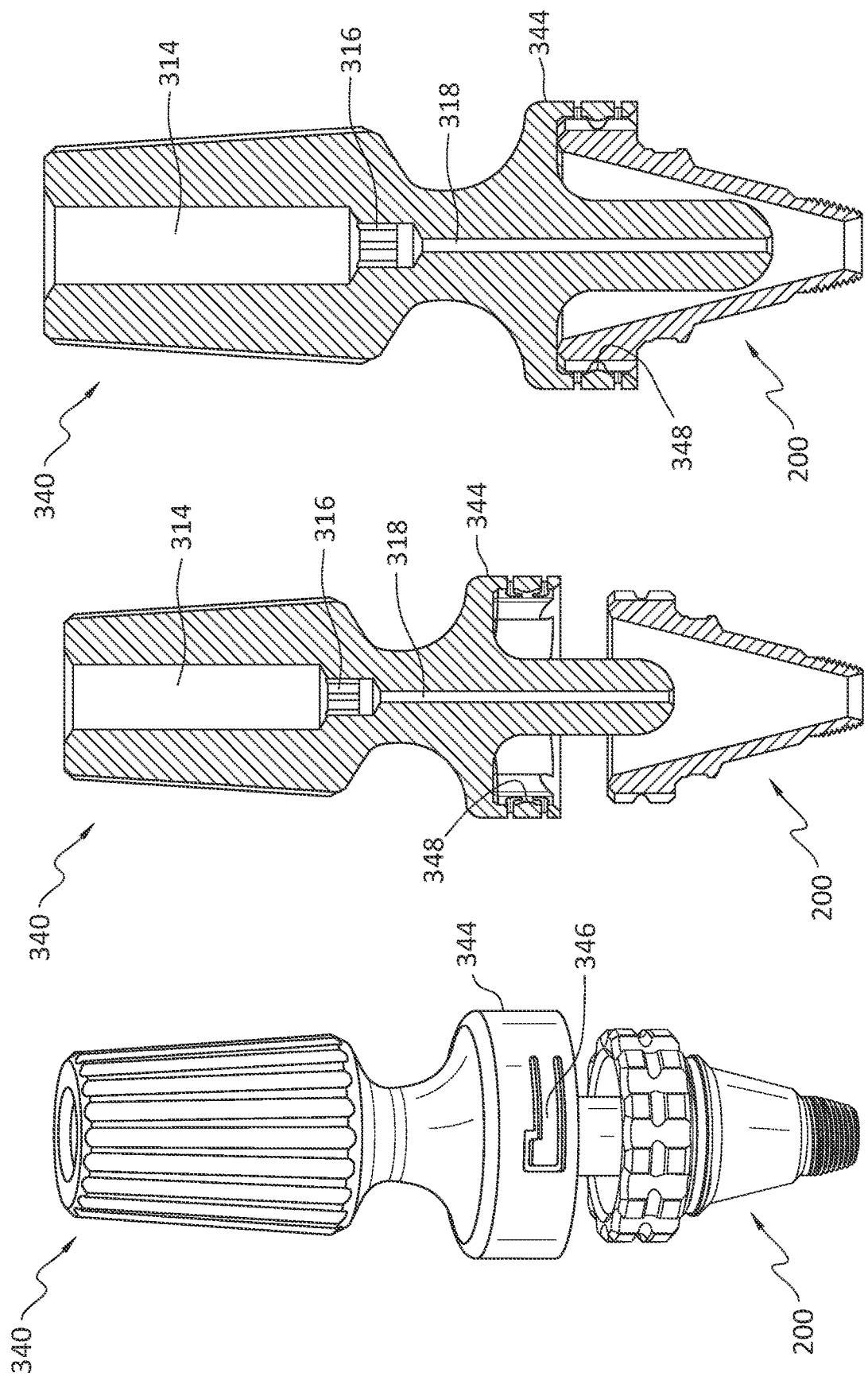

VARIABLE ANGLE DRILL GUIDE

TECHNICAL FIELD

Various exemplary embodiments disclosed herein relate generally to a variable angle drill guide, drill guide handles, and tools that help align the drill bit in a desired direction.

BACKGROUND

Bone plates are widely used to secure bone fractures. Such bone plates include a number of plate holes, and screws are inserted through the plate holes into the bone and/or bone fragments to be repaired. Typically a surgeon will use a drill guide to accurately drill holes in the bone to receive the screws used to secure the bone plate to the bone. The drill guide ensures that a hole drilled in the bone is axially aligned with the plate hole in the bone plate or at some other desired angle. Variable angle (VA) locking screws have been developed that allow for the insertion of the screw that secures the bone plate at various angles.

Variable angle locking screws provide the ability to create a fixed-angle construct while also allowing the surgeon the freedom to choose the screw trajectory. A fixed-angle construct provides advantages in osteopenic bone or multi-fragmentary fractions. With variable angle (VA) screw technology, screw angulation is unlimited with a specified cone angle around the central axis of the bone plate hole. VA screws enable optimal screw positioning and offers many benefits by allowing the surgeon to: target fragments with high-quality bone, especially in patients with osteopenic bone; adjust screw direction after bending the plate; position screws precisely to avoid joint penetration; redirect screw position to avoid existing implants, prostheses, or independent lag screws; and adapts screw position to accommodate varied patient anatomy and capture fracture fragments.

SUMMARY

A summary of various exemplary embodiments is presented below. Some simplifications and omissions may be made in the following summary, which is intended to highlight and introduce some aspects of the various exemplary embodiments, but not to limit the scope of the invention. Detailed descriptions of an exemplary embodiment adequate to allow those of ordinary skill in the art to make and use the inventive concepts will follow in later sections.

Various embodiments relate to an drill guide handle configured to engage a variable angle drill guide, including: a handle grip; a first cannula extending from a proximal end of the drill guide handle to a distal end of the drill guide handle, wherein the first cannula is configured to provide a zero degree insertion angle for a drill bit; and a body including: a first tab and a second tab wherein the first and second tabs include a first and second tab protrusion, respectively, wherein each of the first tab and the second is configured to flex so that the first and second tab protrusions engage a horizontal groove on a variable angle drill guide; and a body protrusion on an inner surface of the body, wherein the body protrusion is configured to engage a vertical grove on the variable angle drill guide.

Various embodiments are described, wherein body includes: first tab border opening configured to form the first tab, wherein an outer surface of the first tab substantially conforms with an outer surface of the body; and second tab border opening configured to form the second tab, wherein an outer surface of the second tab substantially conforms with the outer surface of the body.

Various embodiments are described, wherein first tab and the second tab extend substantially along a direction of an axis of the cannula from the proximal end to the distal end of the drill guide handle.

Various embodiments are described, wherein first tab and the second tab extend in a direction substantially perpendicular to an axis of the cannula from the proximal end to the distal end of the drill guide handle.

Various embodiments are described, wherein the first tab and the second tab extend substantially away from the body in a direction of an axis of the cannula from the proximal end to the distal end of the drill guide handle.

Various embodiments are described, wherein the body further includes a first tab stop configured to limit the flexing motion of the first tab; and a second tab stop configured to limit the flexing motion of the second tab.

Various embodiments are described, wherein the cannula includes a proximal cannula portion and a distal cannula portion, wherein the cross-sectional size of the proximal cannula portion is larger than the cross-sectional size of the distal cannula portion.

Various embodiments are described, wherein proximal cannula portion is configured to accept a driver.

Various embodiments are described, wherein further includes a middle cannula portion with a cross-sectional shape complementary to the end of the driver, wherein the middle cannula section is configured to grip the end of the driver.

Various embodiments are described, wherein cross-sectional area of the distal cannula portion configured to accommodate a drill bit passing therethrough.

Various embodiments are described, wherein the body has bottom edge with a chamfer on the inner side.

Various embodiments are described, further including a second cannula extending from the proximal end of the drill guide handle to the distal end, wherein the second cannula configured to provide a insertion angle for a drill bit having a second angle and wherein the distal end of the second cannula intersects with the distal end of the first cannula.

Various embodiments are described, further including a third cannula extending from the proximal end of the drill guide handle to the distal end, wherein the third cannula configured to provide a insertion angle for a drill bit having a third angle and wherein the distal end of the third cannula intersects with the distal ends of the first cannula and the second cannula.

Various embodiments are described, further including a drill guide stop inside the body configured to stop the drill guide when engaged with the drill guide handle and configured to align the first and second tabs with the horizontal grooves.

Various embodiments are described, wherein the variable angle drill guide includes: a frustoconical body with a first opening at a narrower distal end and second opening at a wider the proximal end; and a grip surrounding the wider proximal end, where the grip includes horizontal grooves and vertical grooves.

Various embodiments are described, wherein the narrower distal end includes threads on an outer surface of the distal end, wherein the thread are configured to engage threads in a plate hole of a bone plate.

Further various embodiments relate to a method of inserting a variable angle drill guide into the bone using the drill guide handle of claim 16, including: connecting the drill guide handle to the variable angle drill guide by sliding the drill guide handle over the grip of the drill guide until the first and second tabs engage the horizontal grooves and where sliding the drill guide handle over the grip further includes aligning the body protrusion with one of the vertical grooves on the grip; screwing the threads of the variable angle drill guide into a plate hole of the bone plate; drilling a hole in the bone by placing the drill bit in the first cannula, wherein the drilled hole is a zero degree insertion angle hole; and unscrewing the threads of the variable angle drill guide from the plate hole of the bone plate.

Various embodiments are described, further including: inserting a driver into the cannula of the drill guide handle prior to screwing the screwing the threads of the variable angle drill guide into a plate hole of the bone plate, wherein screwing the threads of the variable angle drill guide into the plate hole of the bone plate includes rotating the driver, and unscrewing the threads of the variable angle drill guide from the plate hole of the bone plate includes rotating the driver.

Further various embodiments relate to a method of inserting a variable angle drill guide into the bone using the drill guide handle from above, including: connecting the drill guide handle to the variable angle drill guide by sliding the drill guide handle over the grip of the drill guide until the first and second tabs engage the horizontal grooves and where sliding the drill guide handle over the grip further includes aligning the body protrusion with one of the vertical grooves on the grip; screwing the threads of the variable angle drill guide into a plate hole of the bone plate; removing the drill guide handle from the variable angle drill guide; drilling a hole in the bone by placing the drill bit in the variable angle drill guide, wherein the drilled hole has an insertion angle other than zero degrees; reconnecting the drill guide handle to the variable angle drill guide; and unscrewing the threads of the variable angle drill guide from the plate hole of the bone plate.

Various embodiments are described, further including: inserting a driver into the cannula of the drill guide handle prior to screwing the screwing the threads of the variable angle drill guide into a plate hole of the bone plate, wherein screwing the threads of the variable angle drill guide into a plate hole of the bone plate includes rotating the driver, and unscrewing the threads of the variable angle drill guide from the plate hole of the bone plate includes rotating the driver.

Further various embodiments relate to a drill guide including: a grip at a proximal end of the drill guide; a frustoconical body connected to the grip; a frustoconical inner opening extending from the proximal end to the distal end, wherein the frustoconical inner opening has a first opening at a narrower distal end and second opening at a wider the proximal end, wherein the drill guide has a first central axis extending from the proximal end to the distal end of the drill guide and wherein the central axis is centered in the drill guide, wherein the frustoconical inner opening has a second central axis extending from the proximal end to the distal end of the frustoconical inner opening that is offset in a first direction from the first central axis in a first direction that is substantially perpendicular to the first central axis; and an indicator on a proximal end of the grip located on a circumference of the proximal end in a direction opposite the first direction.

Various embodiments are described, further including: a handle configured to removably connect to the drill guide.

Further various embodiments relate to a drill guide handle configured to engage a variable angle drill guide, including: a handle grip; a first cannula extending from a proximal end of the drill handle to a distal end of the drill guide handle, wherein the first cannula is configured to provide a zero degree insertion angle for a drill bit; and a body including: an inner groove extending around an inner circumference of the body; a canted coil spring in the inner groove, wherein the canted coil spring is configured to flex so that the canted coil spring engages a horizontal groove on a variable angle drill guide; and a body protrusion on an inner surface of the body, wherein the body protrusion is configured to engage a vertical grove on the variable angle drill guide.

Further various embodiments relate to a drill guide, including: a frustoconical body with a first opening at a narrower distal end and second opening at a wider the proximal end; and a grip surrounding the wider proximal end wherein a plurality of angle indicators are placed on a proximal end of the grip.

Further various embodiments relate to a drill guide, including: a frustoconical body with a first opening at a narrower distal end and second opening at a wider the proximal end; and a grip surrounding the wider proximal end, wherein a plurality of angle indicators are placed on an inner surface at a proximal end of the grip.

Further various embodiments relate to a drill guide assembly configured to limit a drill angle, including: a circular body with a central opening, wherein the circular body is configured to engage a variable angle drill guide; an adjustment ring attached to the circular body; a plurality of leaves attached to the circular body, wherein the plurality of leaves form a variable aperture, the leaves open and close the variable aperture when the adjustment ring is rotated, and the variable aperture limits the drill angle.

Further various embodiments relate to a drill angle guide configured to be placed over a drill bit, including: a flat disk with a central opening, wherein the central opening is configured to accept the drill bit and the flat disk is transparent; a plurality of insertion angle rings on the flat disks indicating different drill angles, wherein the insertion angle rings are centered on the central opening, and a plurality of orientation lines on the flat disk indicating different drill orientation angles, wherein the orientation lines extend radially from the central opening to an outer edge of the flat disk.

BRIEF DESCRIPTION OF THE DRAWINGS

In order to better understand various exemplary embodiments, reference is made to the accompanying drawings, wherein:

FIGS. 1A-E illustrate top perspective, side, cross-sectional, top, and bottom views, respectively, of an embodiment of a variable angle offset drill guide that facilitates zero degree and variable angle drilling in compression plates;

FIGS. 7A-F illustrate top perspective, bottom perspective, side, cross-sectional, top, and bottom views, respectively, of another embodiment of a drill guide handle;

FIGS. 8A-C illustrate a prospective and two cross-sectional views of another embodiment of a drill guide handle;

Figure 13:
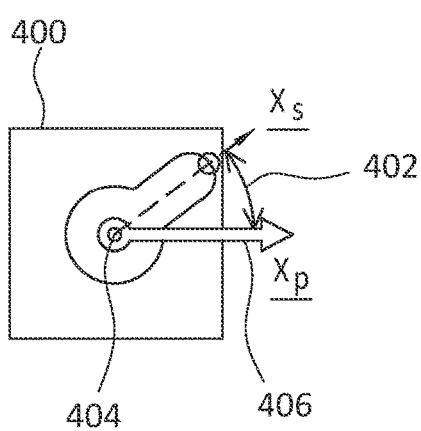
Figure 14:
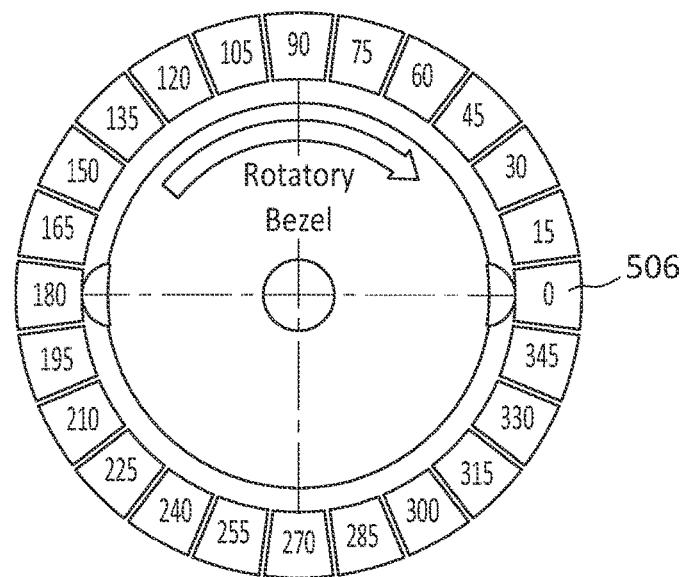
Figure 15:
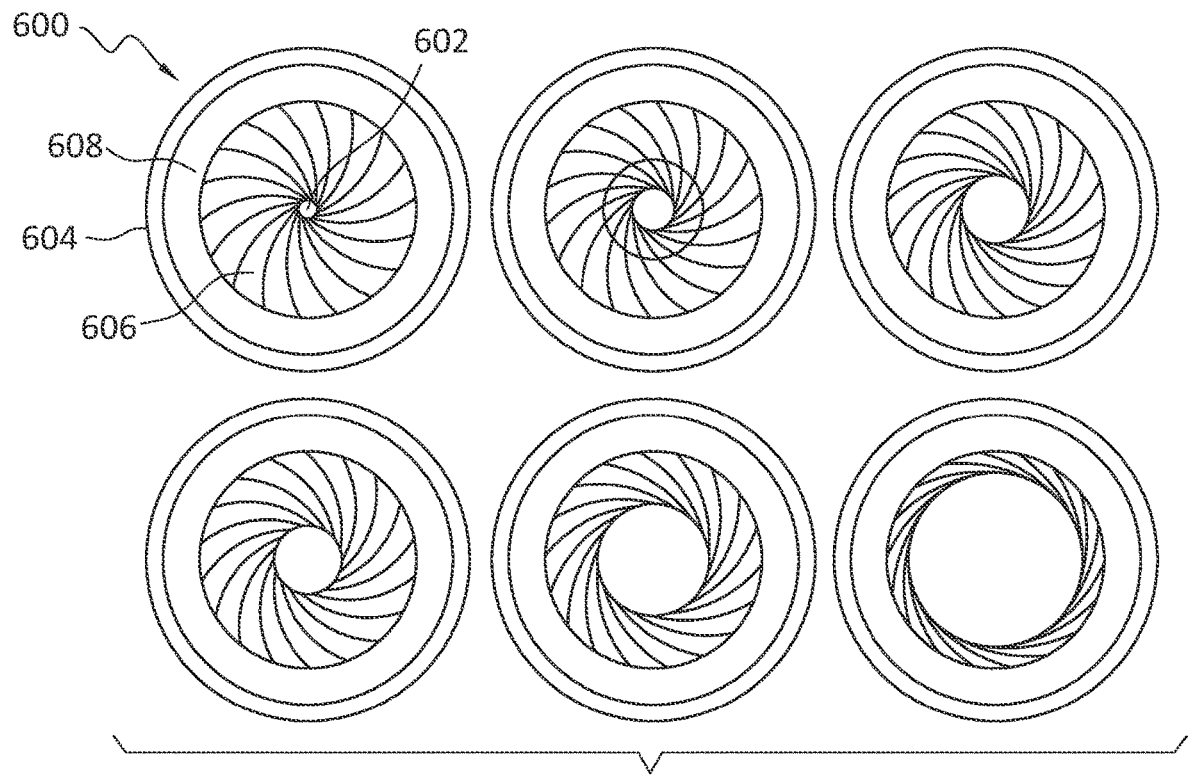
Figure 16:
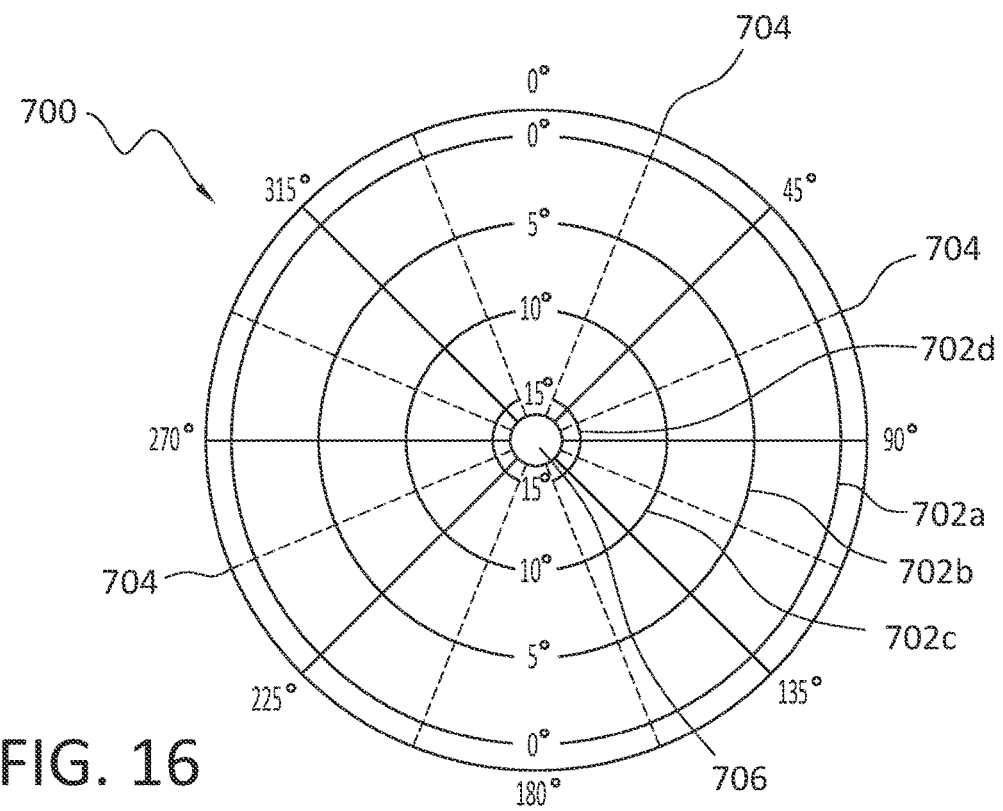
Figure 17:
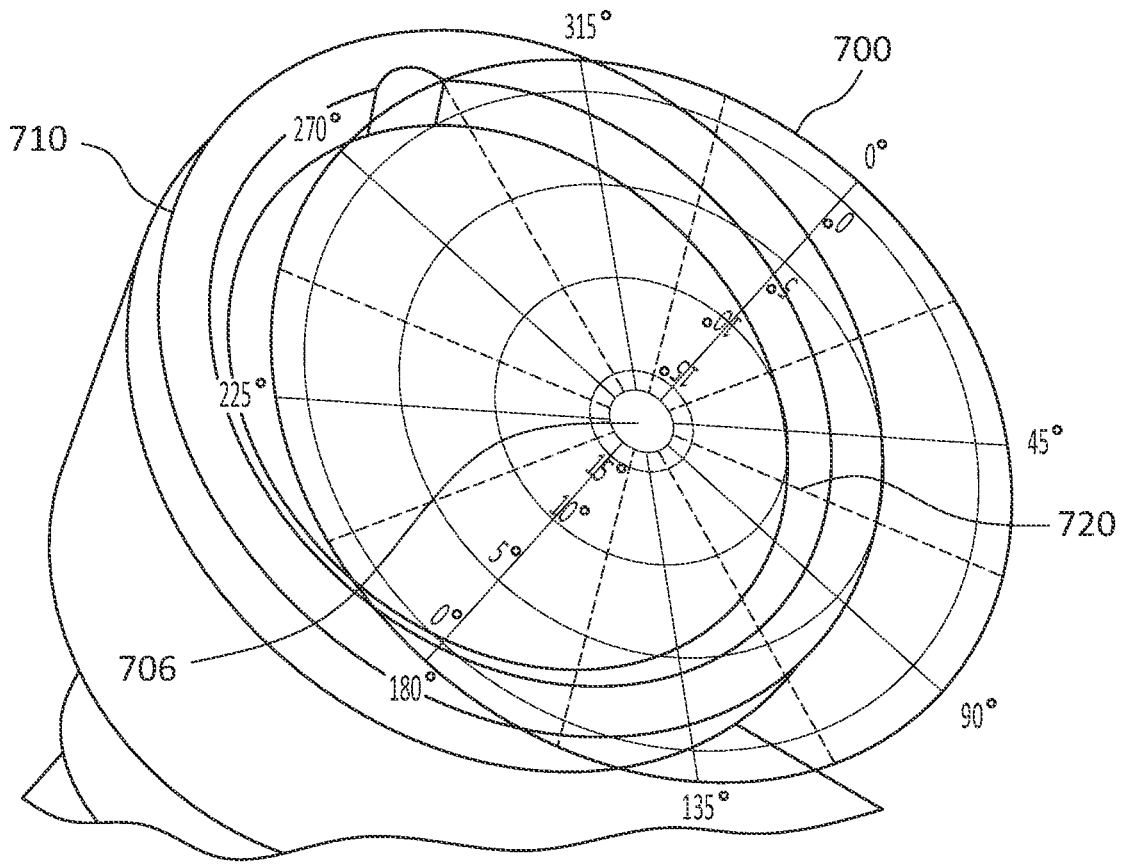
Figure 18:
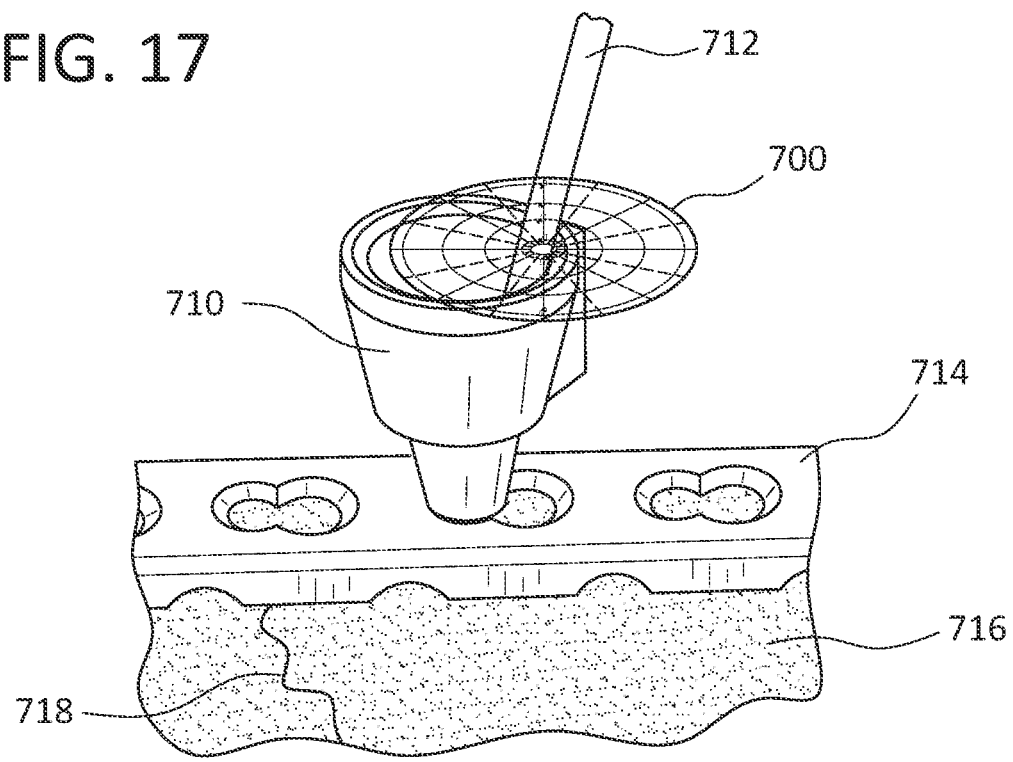

12B illustrates just the proximal end of an embodiment of the drill guide handle;

12C illustrates another embodiment of the distal end of the drill guide handle;

FIG. 13 helps to illustrate a rotation angle;

FIG. 14 illustrates that markings that may be placed on a drill guide or on a bezel of a drill guide;

FIG. 15 illustrates an embodiment of a variable aperture attachment;

FIG. 16 illustrates drill angle template for use with a variable angle drill guide; and FIG. 17 illustrates the drill angle template placed on the proximal end of a drill guide; and FIG. 18 illustrates a drill bit inserted through the drill angle template 700 and the drill guide.

To facilitate understanding, identical reference numerals have been used to designate elements having substantially the same or similar structure and/or substantially the same or similar function.

DETAILED DESCRIPTION

The description and drawings illustrate the principles of the invention. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments.

When VA screws are used, a drill guide may be used to limit the insertion angle of hole drilled in the bone. The insertion angle may be defined as the angle from a normal axis to a plate hole in a bone plate configured to accept a screw. At the same time, in some situations it is desired that the VA or other screws are inserted with a zero degree angle. A zero degree angle hole includes a hole that substantially aligns with the axis of the plate hole in the bone plate. A drill guide may be used to accommodate the precise drilling of such a hole. Accordingly, there is a need for a drill guide that provides the surgeon the options of drilling a zero degree angle (i.e., drilling coaxially with the axis of the plate hole) hole or a hole at an insertion angle off the axis of the plate hole that is within an angle limit. Such a device will replace the need for two different drill guides, i.e., one for zero degree angle holes and one that limits the insertion angle of holes to a desired angular limit. Various embodiments of variable angle drill guides, drill guide handles, and other accessories will be described below that facilitate the drilling of zero degree and variable angle holes in the bone. An example of a variable angle drill guide is found in U.S. patent application Ser. No. 17/011,425 filed on Sep. 3, 2020, entitled "DRILL GUIDE WITH INTEGRATED VARIABLE ANGLE AND ZERO DEGREE DRILLING," which is hereby incorporated by reference for purposes as if included herein.

Further, compression plates may be used in order to assist in compressing a bone fragment in order to reduce a facture. Compression plates have plate holes that have an opening that are larger at the surface of the plate and that reduce in size with a compression portion including a sloping or other surface that engages the head of the screw. A bone screw or other fixation element inserted into the plate hole in the compression plate imparts a force to the bone plate to move the bone plate laterally relative to a portion of bone into which the bone screw is inserted. This allows for compression and reduction of bone fragments attached to the compression plate. Such plate holes may also accommodate VA screws allowing the VA screws to be inserted at various angles as required in order to treat and secure a specific fracture. These plate holes may have a first opening portion that is rounded or semi-spherical to facilitate the insertion of VA screws at various angles.

It takes thought and planning to visualize how the screw hole needs to be offset in the plate hole relative to the bone fraction to be compressed and reduced. Embodiments of a drill guide will be described that help facilitate drilling offset holes for compression plates with various insertion angles.

FIGS. 1A-E illustrate top perspective, side, cross-sectional, top, and bottom views, respectively, of an embodiment of a variable angle offset drill guide that facilitates zero degree and variable angle drilling with compression plates. The drill guide 100 includes a grip 104. The drill guide 100 is generally of a frustoconical shape as shown by an frustoconical wall defined by outer surface 110 and inner guide surface 120. The inner guide surface 120 defines a frustoconical inner opening 124. The drill guide 100 includes a proximal end with a proximal edge 102 and a distal end with a distal edge 114. The distal end is configured to engage a plate hole on the bone plate. This may be facilitated by a proximal step 122 on the outer surface 110. The proximal step 122 is sized to engage the surface of the plate around the plate hole on the bone plate or a stop surface in the plate hole. This proximal step 122 will ensure that the drill guide 110 is securely engaged with the bone plate while screw holes are drilled in the bone. In other embodiments the distal end of the drill guide 100 may be rounded or semi-spherically shaped to engage plate holes that have such a complementary shape.

The distal end of the drill guide 100 also includes a distal opening 116 through which the drill bit passes in order to drill into the bone. The proximal end of the drill guide 100 includes a proximal opening 106.

FIG. 1C illustrates a cross-sectional view of the drill guide 100 that shows angular limits on the drill bit when using the drill guide. The frustoconical inner opening 124 has angular limits that limit the largest insertion angle that a surgeon can select when drilling a screw hole. For example, the frustoconical inner opening 124 may span 10°, 20°, or 30° that allows for up to 5°, 10°, and 15° screw insertion angles. Different drill guides 100 with different maximum insertion angles may be available to the surgeon who may select the drill guide 100 that meets the operational needs.

The drill guide 100 may also include a direction indicator 108 that assists the user of the drill guide 100 to align the drill guide to facilitate drilling the screw hole to allow for compression of the attached bone fragments. The direction indicator 108 may be an arrow or some other shape that is placed on the proximal edge 102 that provides a visual indication for the surgeon to use to orient the drill guide 100. The direction indicator 108 may also include wording or letters and may be made of a distinct color to stand out. Further, direction indicator may be printed, etched, or embossed on the proximal edge 102. When the drill guide 100 is used to drill the screw hole, the direction indicator is rotated in the plate hole so that it points to the fracture. FIG. 1C illustrates the drill guide oriented so that the direction indicator 108 is on the left. In this configuration, the frustoconical inner opening 124 is shown as laterally shifted to the right from a center axis running between the proximal end and distal end of the drill guide 100. This shift in the frustoconical inner opening 124 results in the screw hole being aligned so as to laterally move the bone plate relative to the bone so that the bone plate moves to the right and/or the bone moves to the left in this configuration. So the direction indicator 108 is placed opposite the lateral shift of the frustoconical inner opening 124.

Figure 2A:
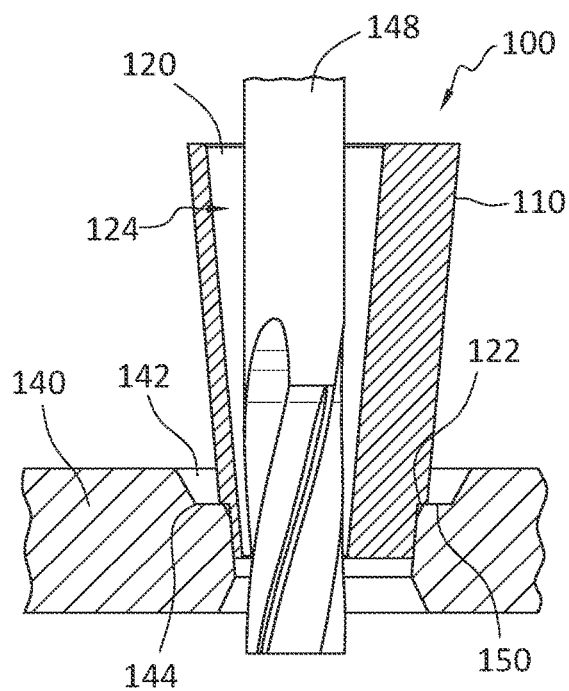
FIGS. 2A-C illustrate drilling a 0° screw hole and inserting a screw to compress a fracture.
Figure 3A:
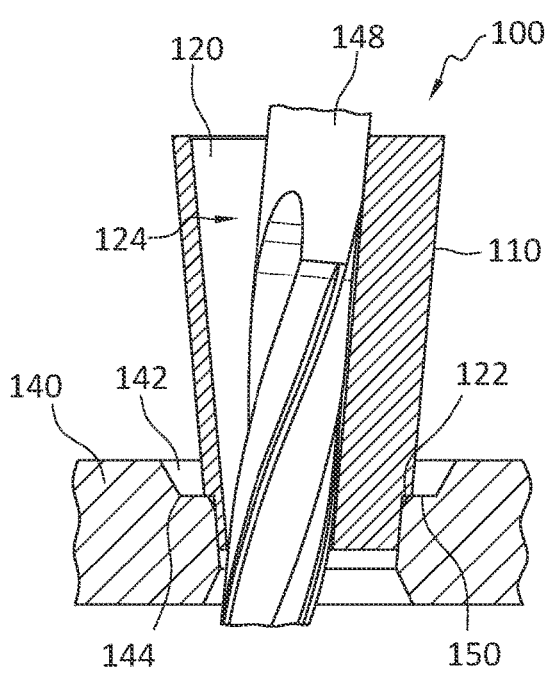
FIGS. 3A-C illustrate drilling a 5° screw hole and inserting a screw to compress a fracture.
Figure 2B:
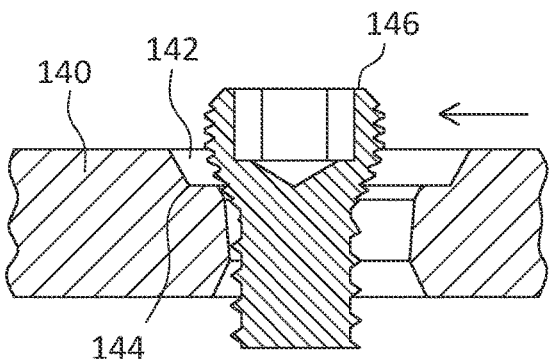
Figure 3B:
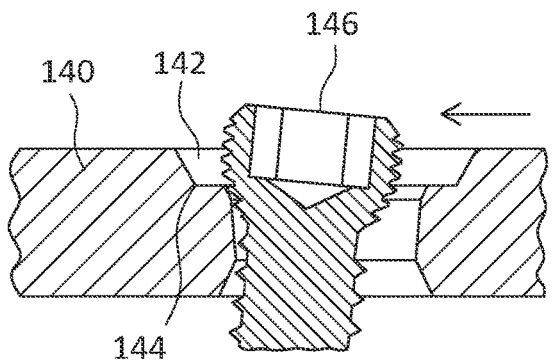
Figure 2C:
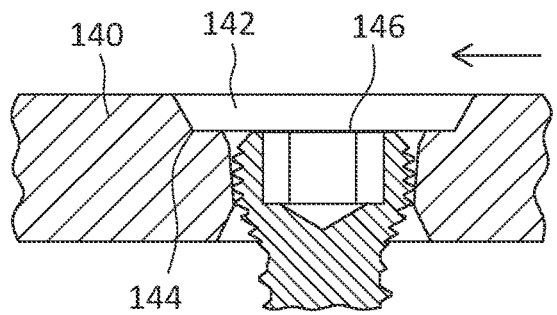
Figure 3C:
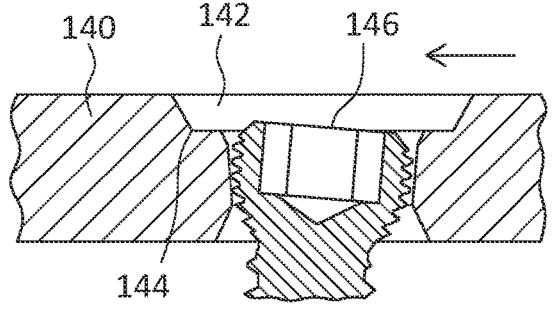

FIGS. 2A-C illustrate drilling a 0° screw hole and inserting a screw to compress a fracture. FIGS. 3A-C illustrate drilling a 5° screw hole and inserting a screw to compress a fracture. In FIG. 2A the drill guide 100 is inserted into the plate hole 142. The proximal step 122 comes to rest on the plate hole stop surface 150. In other embodiments, the size and configuration of the proximal step 122 may cause the proximal step 122 rest on the top surface of plate hole stop surface 150. In FIG. 2A a drill bit 148 is centered in the drill guide 100 and a hole is drilled into the bone with a 0° insertion angle. FIG. 3A is similar to FIG. 2A, but instead the drill bit drills a hole with a 5° insertion angle. FIGS. 2B and 3B illustrate a screw 146 partially inserted into the bone and the plate hole 142. A lower surface of the screw head comes into contact with the bone plate (in this specific example plate hole stop surface 150), and as the screw progresses into the bone, the compression plate 140 moves to the left based upon the geometry of the screw head and the plate hole 142. In FIGS. 2C and 3C the screw 146 is illustrated as fully inserted and the plate has moved to the left. In this situation, the facture in the bone is off to the right, so this leftward movement of the compression plate 140 as the screw 146 is inserted causes the bone fragments attached to the compression plate 140 to compress together to reduce the fracture. Further, the drill guide is oriented so that the direction indicator 108 is on the right towards the bone fracture.

Figure 4A:
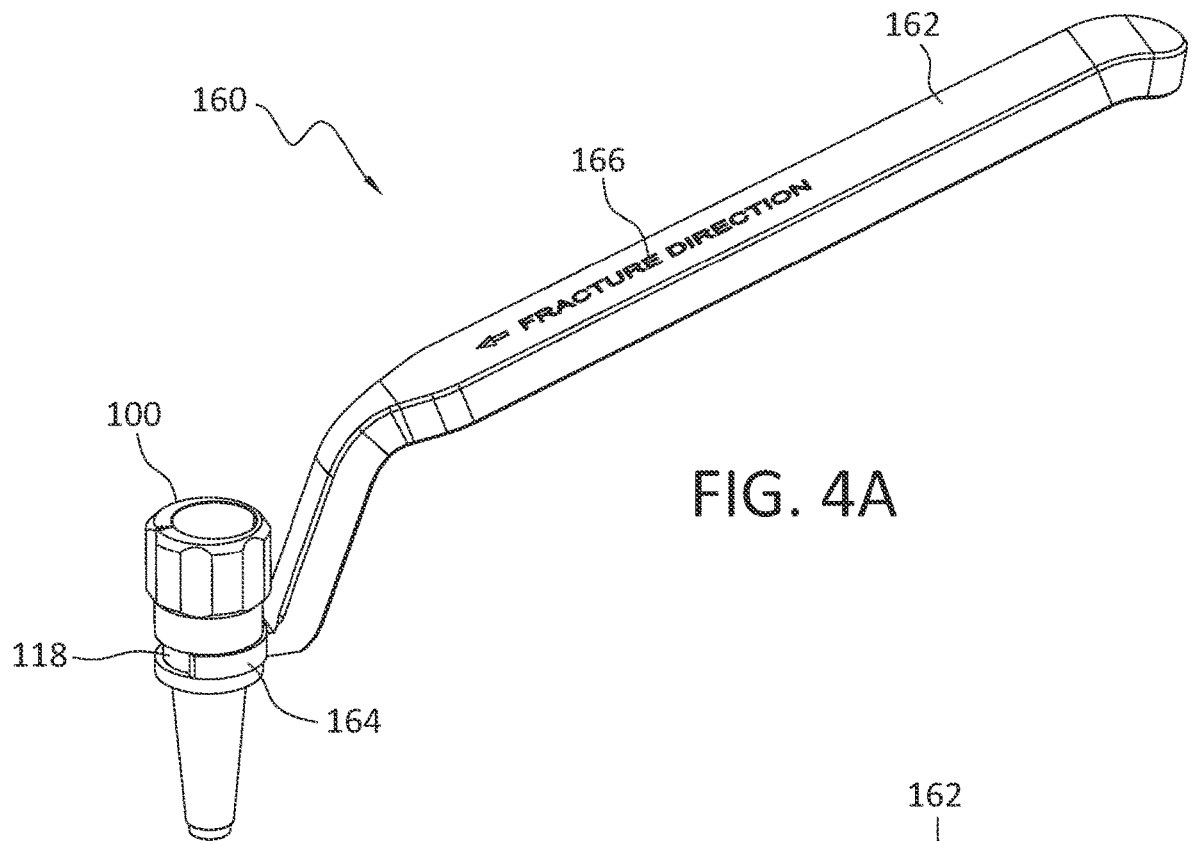
FIGS. 4A-E illustrate a drill guide handle.
Figure 4B:
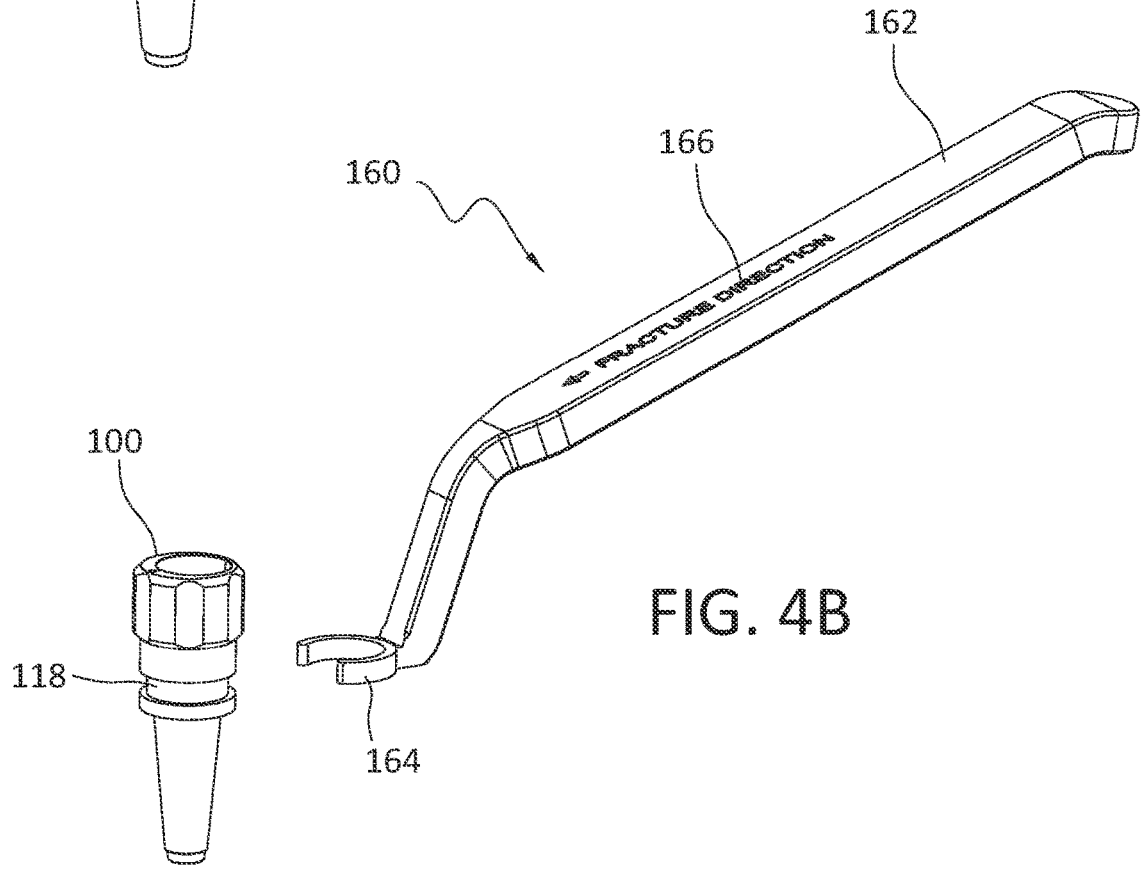
Figure 4C:
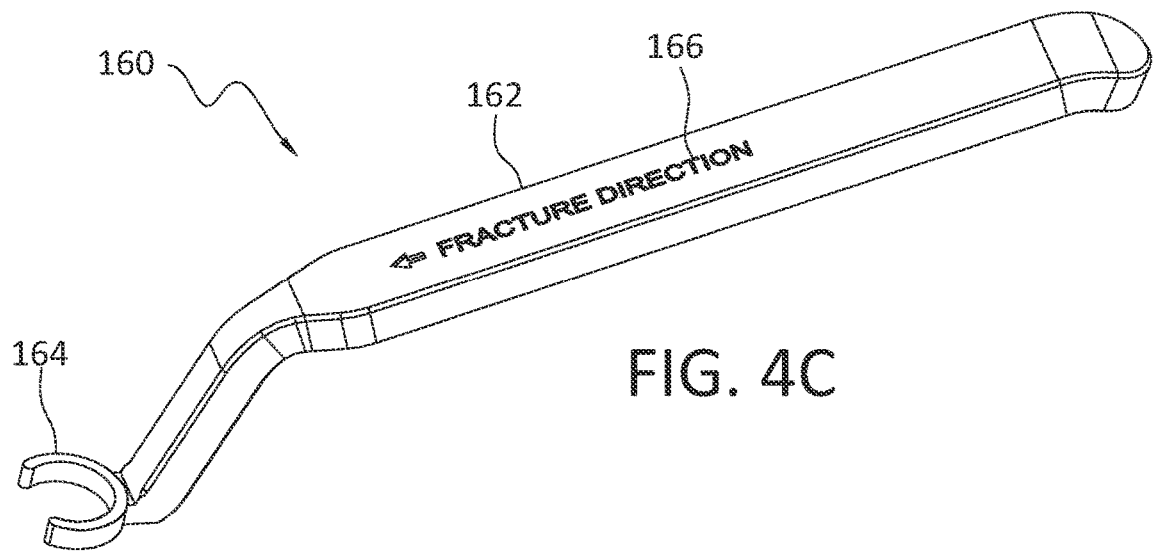
Figure 4D:
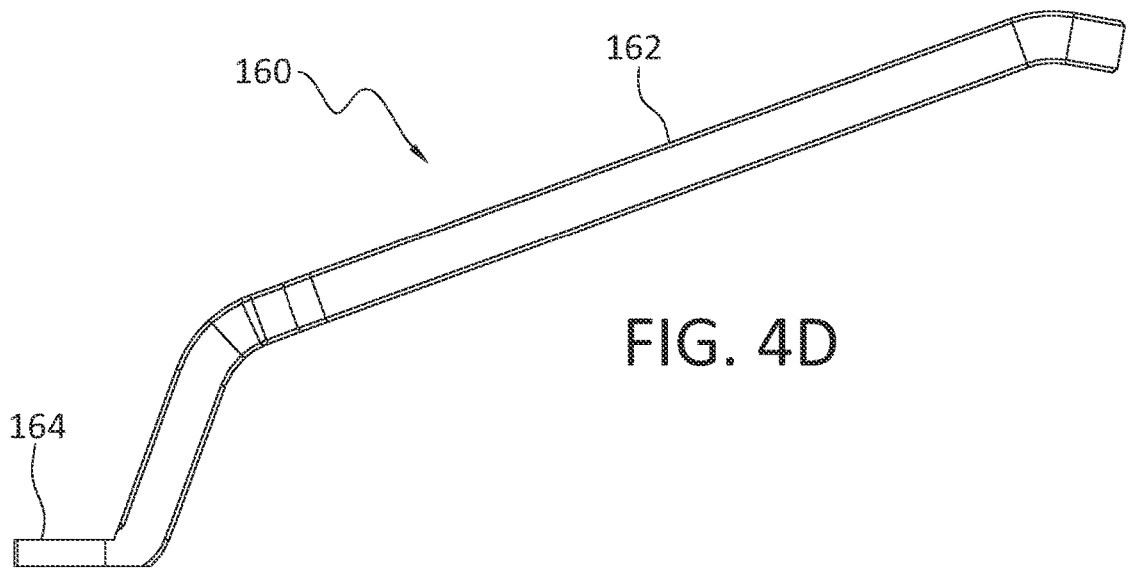
Figure 4E:
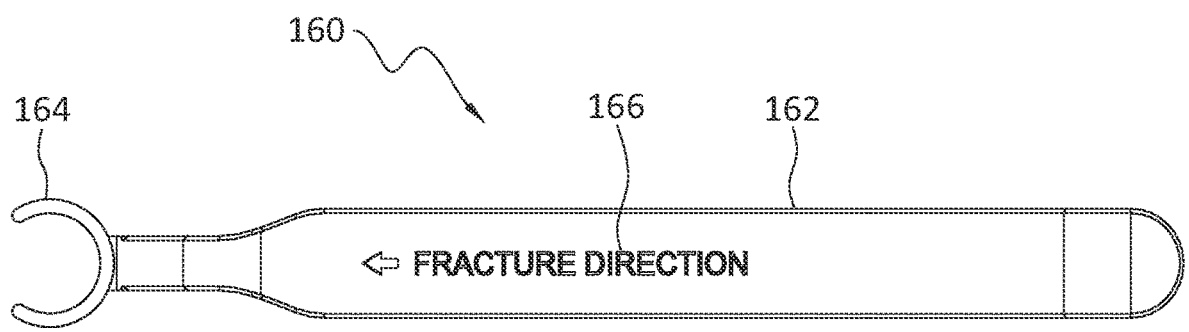

FIGS. 4A-E illustrate a drill guide handle. The handle 160 engages the drill guide 100 so that a surgeon can hold the handle 160 to place the drill guide 100 in the plate hole 142 on the compression plate 140. The handle 160 includes a grip 162, a drill guide engagement member 164, and a handle direction indicator 166. The grip 162 is shown as have a modified L-shape, but could be straight or have other shapes as well. The drill guide engagement member 164 is show a semi-circular clip attached to the end of the grip 162. The drill guide engagement member 164 is flexible so that it can be engaged with the annular groove 118 on the drill guide. The surgeon may easily attach the handle 160 to the drill guide 100 when needed. The grip further may include a handle direction indicator 166. It functions like the direction indicator 108 on the drill guide so that the drill guide is oriented in the correct direction to facilitate compression of the bone fracture. When the handle 160 engages the drill guide 100, the drill guide may be rotated so that the direction indicator 108 and handle direction indicator 166 point in the same direction. In an alternative embodiment, the annular groove 118 may include stops that allows the drill guide engagement member 164 to only engage the drill guide 100 so that the direction indicator 108 and handle direction indicator 166 align. FIG. 4A illustrates the handle 160 engaged with the drill guide 100, and FIG. 4B illustrates the handle 160 disengaged from the drill guide 100.

Figure 5A:
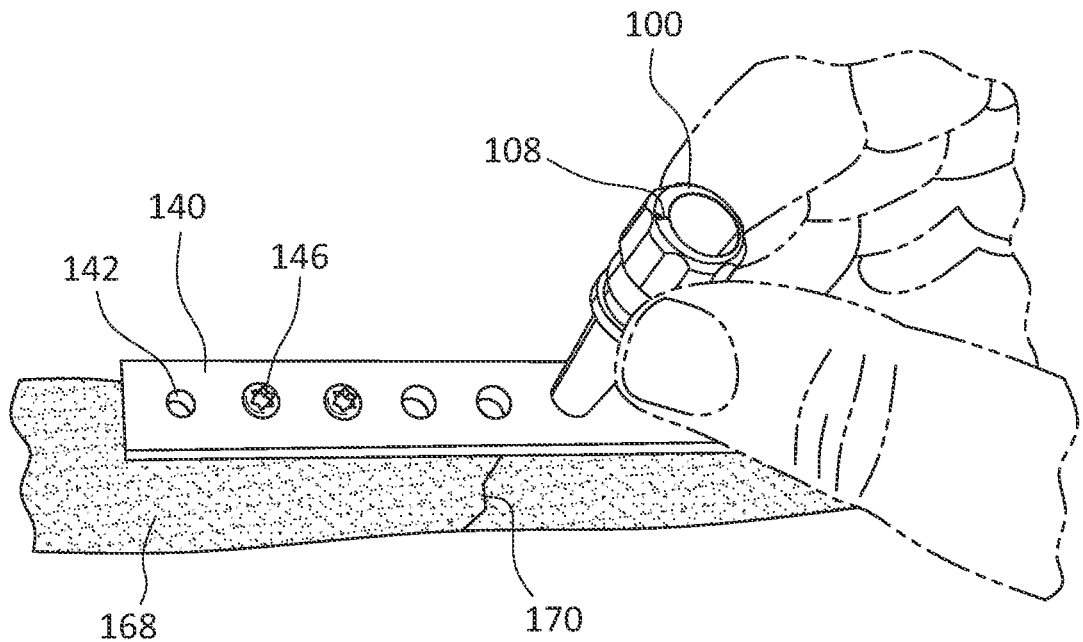
FIGS. 5A and 5B illustrate the placement of the drill guide in a plate hole of a compression plate with and without the handle.
Figure 5B:
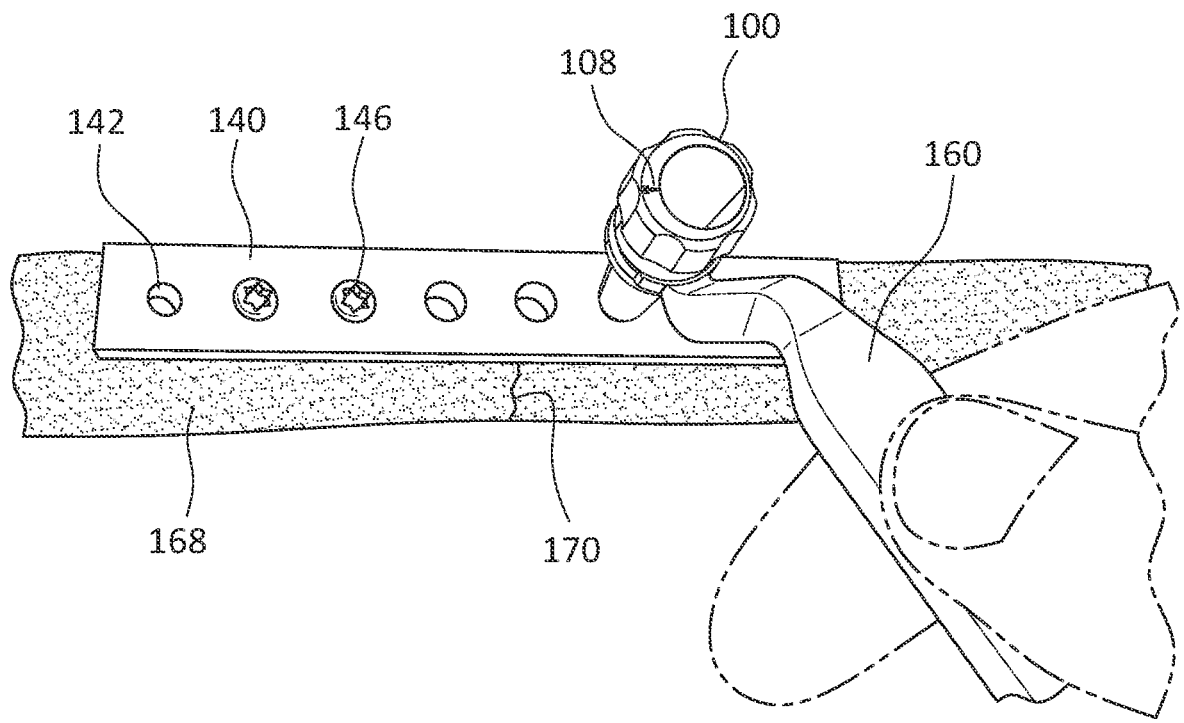

FIGS. 5A and 5B illustrate the placement of the drill guide in a plate hole of a compression plate with and without the handle. In FIG. 5A the surgeon selects the variable angle offset drill guide to drill the hole and to allow for compression of the fracture. The surgeon grips the drill guide grip 104 and places the drill guide in the plate hole 142. In this example, the compression plate 140 has already been secured to a portion of the bone 168 on the left side of the bone fracture 170. The surgeon rotates and places the drill guide 100 in the plate hole 142 so that the direction indicator 108 points towards the bone fracture 170 as illustrated. Next, the surgeon drills a hole in the bone at a desired angle using the drill guide 100. As a result, the hole drilled in the bone is correctly offset. Next, the surgeon inserts a screw into this drilled offset hole. Then the surgeon screws a screw into the offset bone hole, and the bone portion on the right moves toward the left to compress the bone portions together and to reduce the bone fracture 170. FIG. 5B is the same as FIG. 5A, but the handle is instead attached to the drill guide 100.

The offset drill guide 100 facilitates the drilling of offset screw holes in the bone to facilitate the use of a compression plate with a bone fracture. It provides a direction indicator that allows the drill guide to be correctly oriented in order to reduce bone fracture.

FIGS. 6A-F illustrate top perspective, bottom perspective, side, cross-sectional, top, and bottom views, respectively, of another embodiment of a drill guide that facilitates zero degree and variable angle drilling with bone plates. The drill guide 200 is generally of a frustoconical shape as shown by an frustoconical wall defined by outer surface 210 and inner surface 220. The inner surface 220 defines a frustoconical inner opening 224. The drill guide 200 includes a proximal end with a proximal edge 202 and a distal end with a distal edge 214. The distal end is configured to engage a plate hole on the bone plate using threads 208. The drill guide 200 may be rotated so that that the threads engage threads in a plate hole. The drill guide 200 may be screwed in until a proximal step 222 on the outer surface 210 engages the surface of the plate around the plate hole on the bone plate. The threads 208 will ensure that the drill guide 110 is securely engaged with the bone plate while screw holes are drilled in the bone.

The distal end of the drill guide 200 also includes a distal opening 216 through which the drill bit passes in order to drill into the bone. The proximal end of the drill guide 200 includes a proximal opening 206.

Figure 6A:
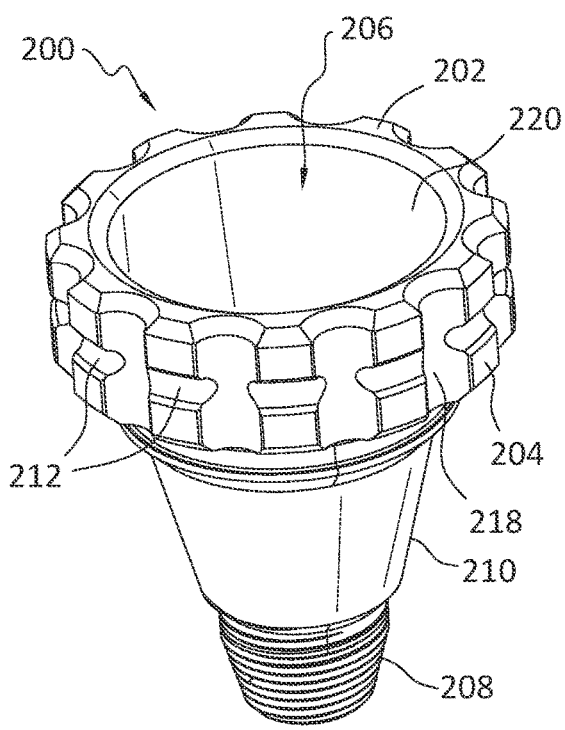
FIGS. 6A-F illustrate top perspective, bottom perspective, side, cross-sectional, top, and bottom views, respectively, of another embodiment of a drill guide that facilitates zero degree and variable angle drilling with bone plates.
Figure 6B:
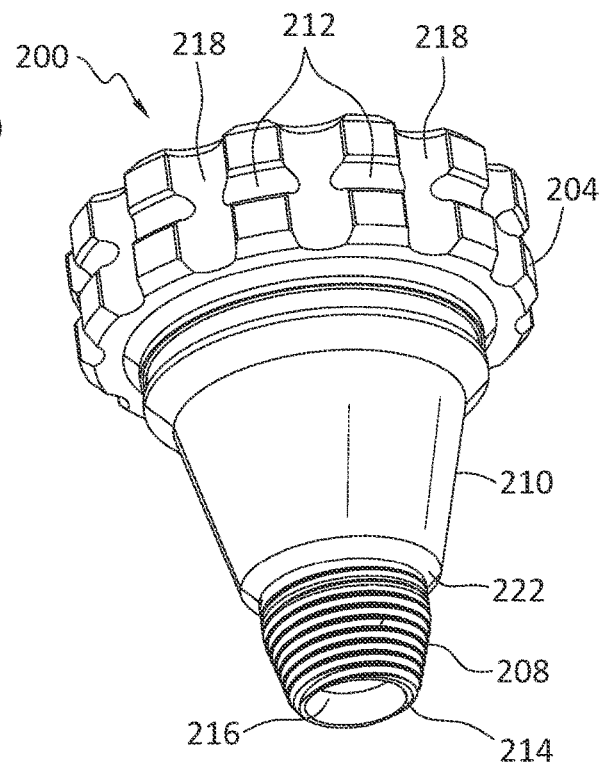
Figure 6C:
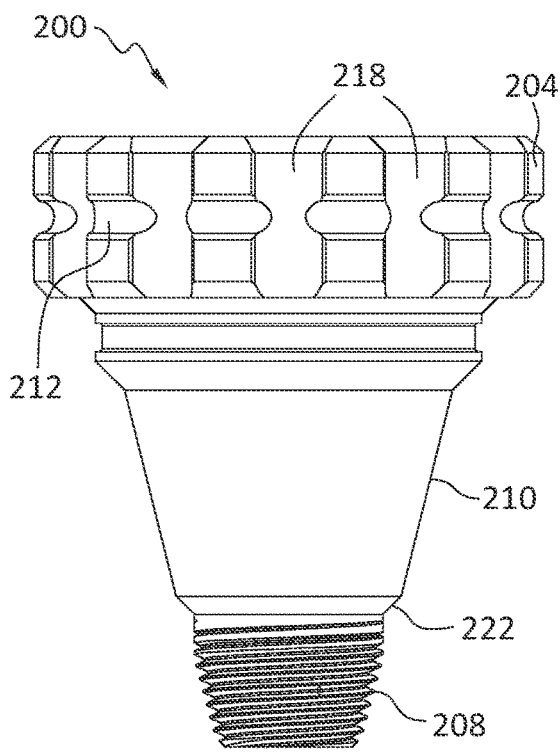
Figure 6D:
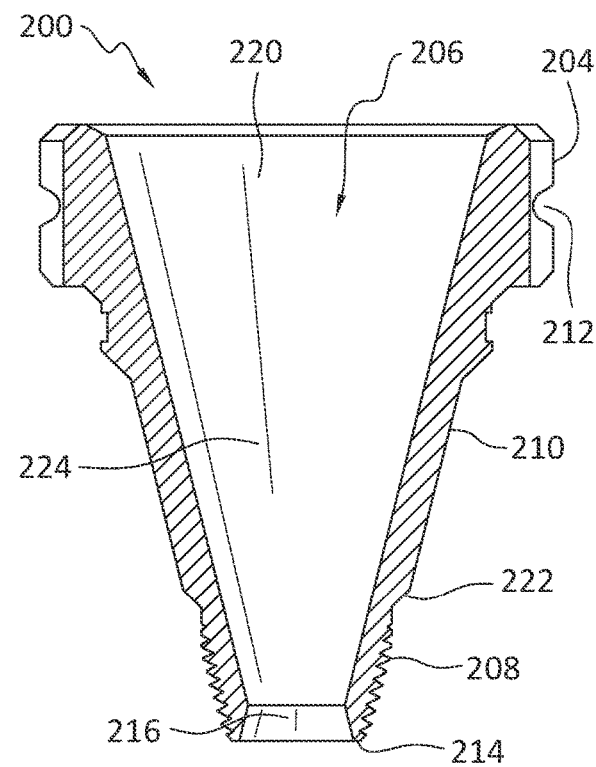
Figures 6E, 6F:
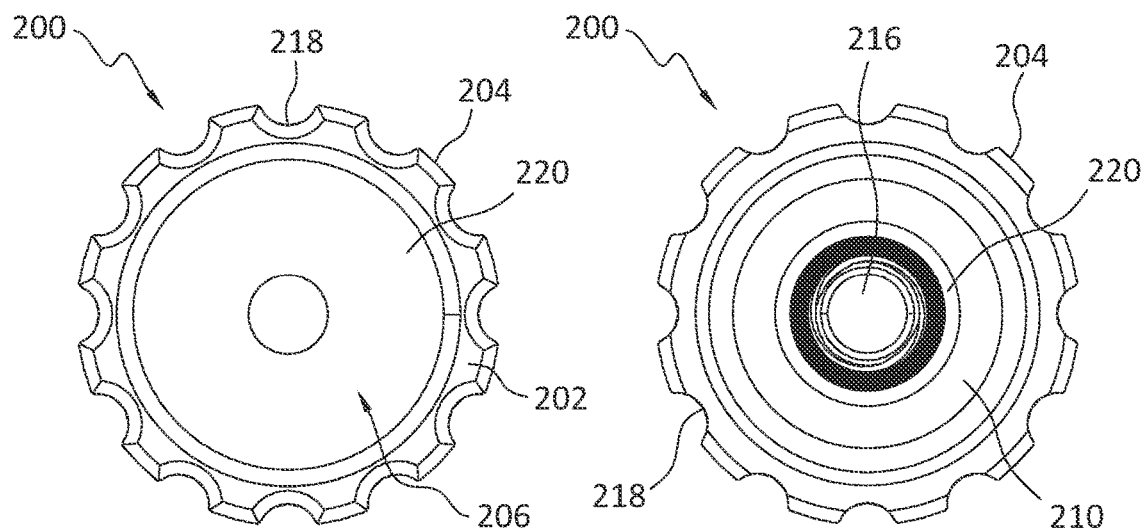
Figures 7A, 7B:
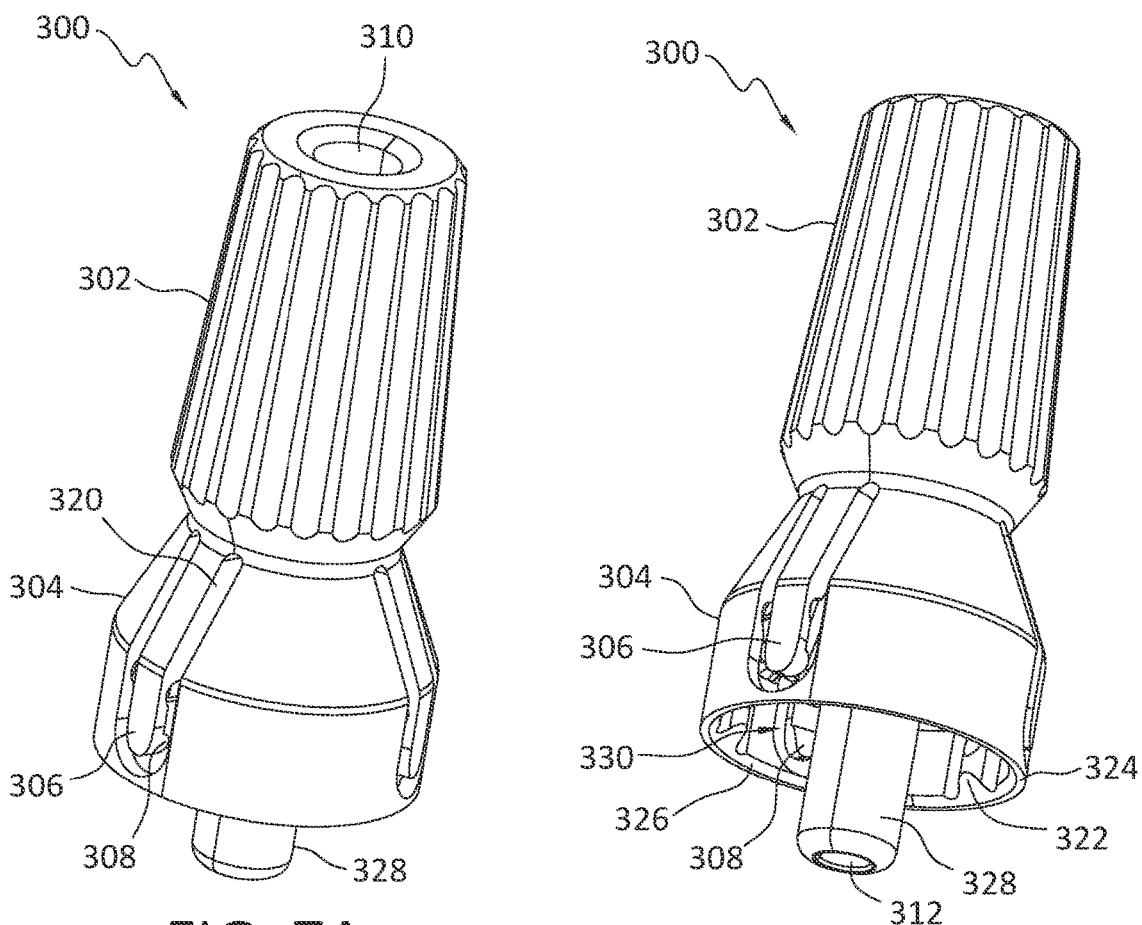

FIG. 6D illustrates a cross-sectional view of the drill guide 200 that shows angular limits on the drill bit when using the drill guide. The frustoconical inner opening 224 has angular limits that limit the largest insertion angle that a surgeon can select when drilling a screw hole. For example, the frustoconical inner opening 224 may span 10°, 20°, or 30° that allows for 5°, 10°, and 15° maximum screw insertion angles. Different drill guides 200 with different maximum insertion angles may be available to the surgeon who may select the drill guide 200 that meets the operational needs.

The drill guide also includes a drill grip guide 204. This grip 204 may be used to grip the drill guide 200 and allow the surgeon in place the drill guide 200 in a plate hole of the bone plate. Further, the grip 204 may include horizontal grooves 212 and vertical grooves 218. These groove improve the grippability of grip 204. The horizontal grooves 212 and vertical grooves 218 also facilitate the connection of a drill guide handle to the drill guide 200.

FIGS. 7A-F illustrate top perspective, bottom perspective, side, cross-sectional, top, and bottom views, respectively, of another embodiment of a drill guide handle. The drill guide handle 300 is configured to securely attach to the drill guide 200 and to allow the surgeon to place the drill guide 200 into a plate hole in the bone plate. The drill guide 200 may be used to attach plates to small bones like those in the hand or foot. As a result the drill guide will be small and will be placed in small incisions through various soft tissue. As a result it may be difficult to directly place the drill guide 200 into a plate hole of the bone plate. The drill guide handle 300 will make the placement of the drill guide 200 easier because it will extend away from the small incision area and allow the surgeon to grip and rotate the drill guide handle 300 to thus place the drill guide 200.

The drill guide handle may have a handle grip 302 and a handle body 304. A proximal end has a proximal opening 310, and a distal end has a distal opening 312. In between the proximal opening 310 and a distal opening 312 is a cannula including an proximal cannula 314, a middle cannula 316, and a distal cannula 318. The cannula accepts a drill bit to facilitate the drilling and screw length determination of a 0° hole in bone when the drill guide handle 300 is connected to the drill guide 200. The distal cannula 318 may be dimensioned to accommodate the largest drill bit to be used to drill the hole in the bone. The proximal cannula 314 may have a larger diameter or cross-sectional area than the distal cannula 318 in order to accommodate the blade of a driver such as a star driver and to ease the transportation of bone chips. The middle cannula 316 may have a shape complementary to the end of the driver and would be star shaped when a star driver is to be used. The driver may be inserted into the proximal cannula 314 and the middle cannula 316 to allow the driver to be used to place or remove the drill guide into the plate hole. Because the middle cannula 316 has a complementary shape to the end of the driver, the driver may be used to rotate the drill guide handle 300 and hence the drill guide 200 so that the threads 208 thread into the plate hole. Then the driver may be removed and the hole may be drilled. This provides the surgeon with even greater reach when working in tight spaces with small incisions.

A central drill guide 328 the houses the distal cannula 318 may extend into and through the handle body 304. The central drill guide 328 has the distal opening 312. In FIGS. 7A-7D, the central drill guide 328 is illustrated as extending beyond the handle body 304, but in other alternatives may not extend from the handle body 304. The length of the distal cannula 318 is selected to provide angular precision needed to drill the 0° hole in the bone and this precision requirement will drive a minimum length of the distal cannula 318.

The handle body 304 extends from the handle grip 302 and forms a body opening 330. The body opening 330 is configured to securely connect to the drill guide handle grip 204. Various features of the handle body 304 facilitate this secure grip. The handle body 304 include tabs 306. Each of the tabs 306 extend downward and have a tab protrusion 308 at its distal end. The bottom of the tab protrusion 308 may have a sloped end surface that slopes up as it extends towards the center of the drill guide handle 300. The drill guide handle 300 illustrates three tabs, but one or more tabs may be used instead. The tab protrusions 308 are configured to engage the horizontal grooves 212 on the drill guide. As the drill guide handle 300 is connected to the drill guide 200, the tab 306 may flex outward as the tab protrusion 308 comes into contact with the proximal edge 202 of the drill guide 200 due to the sloped end surface of the tab protrusion 308. As the drill guide handle 300 continues downward, the proximal edge 202 of the drill guide 200 comes into contact with a drill guide stop surface 332 inside the handle body 304. At this point, the tab protrusion 308 becomes aligned with the horizontal grooves 212 in the drill guide and then snap back towards their original position so that the tab protrusion 308 engages the horizontal grooves 212 to secure the drill guide handle 300 to the drill guide 200. Further, when sufficient upward force is applied to the drill guide handle 300, the tab 306 will flex outward so that the drill guide handle may be removed from the drill guide 200. The tabs 306 may be formed and/or surrounded by a tab border opening 320. In such an embodiment, the outer surface of the tabs substantially conform to shape of the outer surface of the body 304.

The handle body 304 also includes body protrusions 322. The body protrusions 322 extend from an inner wall of the handle body 304 towards the center of the drill guide handle 300. The body protrusions 322 are configured to align with and engage the vertical grooves 218 of the drill guide 200. This engagement allows the drill guide handle 300 to rotate the drill guide 200 when the drill guide 300 is rotated. The body protrusions 322 are spaced so that they simultaneously align with the vertical grooves 218. Further, the location of the body protrusions 322 are selected so that the tap protrusions 308 align with and engage the horizontal groves 218. Three body protrusions 322 are shown but one or more body protrusions may be used.

The handle body 305 also includes a body edge 324 and a body chamfer 326. The body chamfer 326 is a sloping surface that slopes upward as it extends inward towards the center of the drill guide handle 300. This body chamfer 326 is also present on the body protrusion 322. This chamfer 326 increases the ease of engaging the drill guide handle 300 to the drill guide 200 because the drill guide handle 300 and the drill guide 200 do not need to be as closely aligned to connect them together. The chamfer 326 will cause drill guide handle 300 and drill guide 200 to align as they are connected.

A method for using the drill guide 200 and the drill guide handle 300 will now be described. The surgeon selects the drill guide to use, and then connects the drill guide handle to the variable angle drill guide. This may be accomplished by sliding the drill guide handle over the grip of the drill guide until the tabs engage the horizontal grooves and at the same time aligning the body protrusion with one of the vertical grooves on the grip. Optionally, the surgeon may insert the driver into the drill guide handle before or after connecting the drill guide handle to the drill guide. Next, the surgeon may screw the threads of the variable angle drill guide into a plate hole of the bone plate. If a zero degree angle is to be drilled the drill guide handle is left in place, otherwise the surgeon removes the drill guide handle from the variable angle drill guide. Then the surgeon drills a hole in the bone by placing the drill bit in either the drill guide handle or the variable angle drill guide. Next, if the drill guide was removed, the surgeon reconnects the drill guide handle to the variable angle drill guide. Again, this may be optional accomplished using the driver. The surgeon then unscrews the threads of the variable angle drill guide from the plate hole of the bone plate. Now, a screw may be placed in the plate hole and screwed into the bone using the driver.

FIGS. 8A-C illustrate a prospective and two cross-sectional views of another embodiment of a drill guide handle. The drill guide handle 340 is similar to the drill guide 300, but the tabs 346 extend horizontally and circumferentially around the handle body 344 so that the tabs 246 substantially conform to the outer surface of the body 344. The tabs 346 include tab protrusions 348 that engage the horizontal grooves 212 of the drill guide 200. Otherwise, the drill guide handle 340 has the same features and operates in the same manner as the drill guide 300.

Figure 9C:
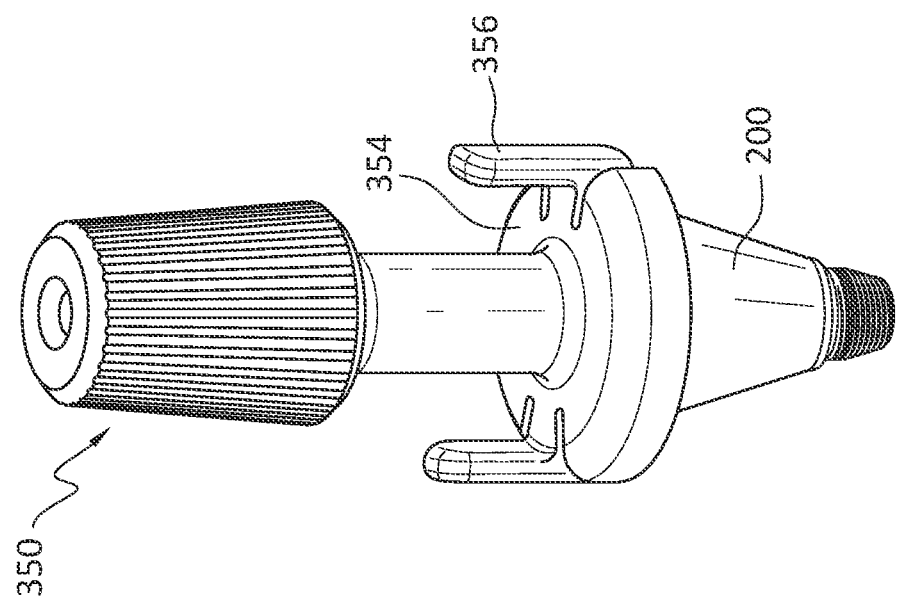
FIGS. 9A-C illustrate a cross-sectional and two perspective views of another embodiment of a drill guide handle.
Figure 9B:
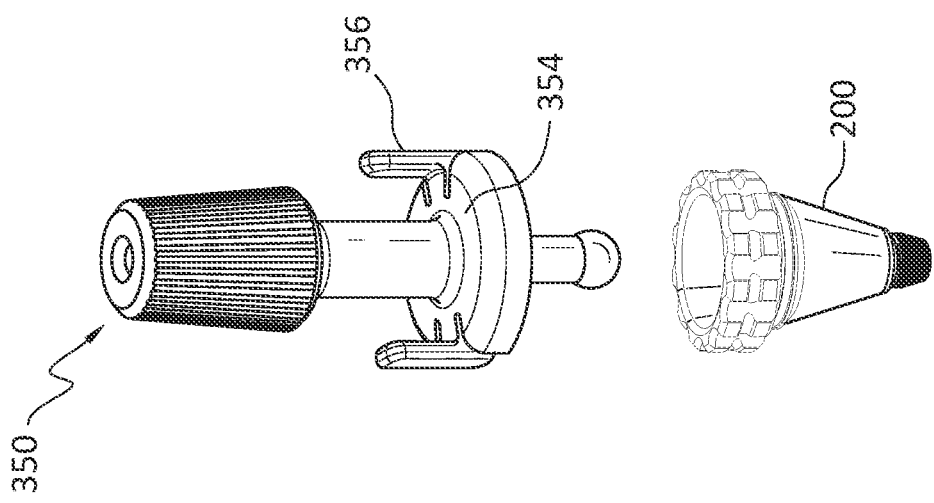
Figure 9A:
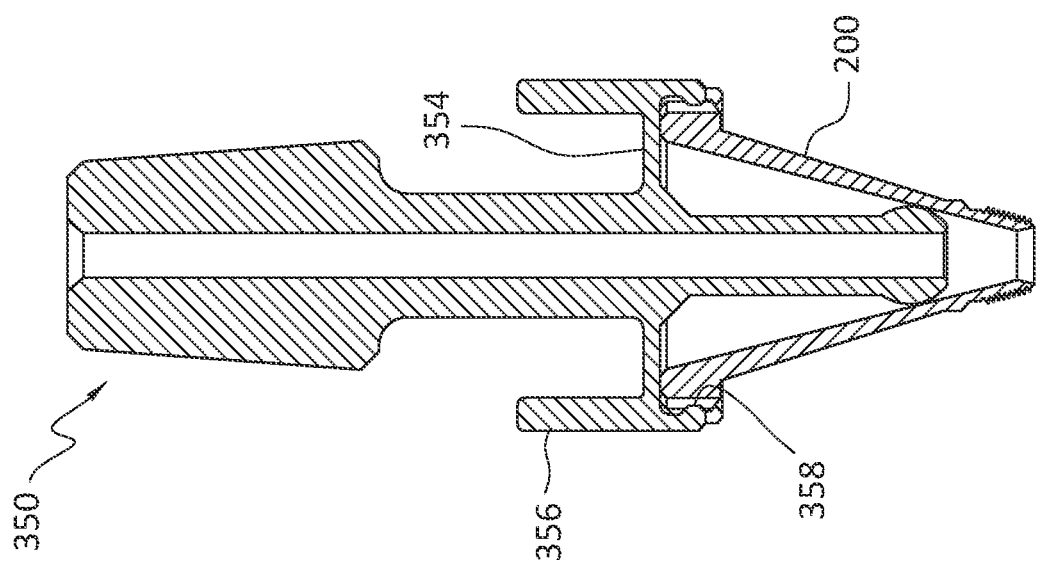

FIGS. 9A-C illustrate a cross-sectional and two perspective views of another embodiment of a drill guide handle. The drill guide handle 350 is similar to the drill guide 300, but the tabs 346 extend upward from the handle body 354. The tabs 356 include tab protrusions 358 that engage the horizontal grooves 212 of the drill guide 200. Otherwise, the drill guide handle 350 has the same features and operates in the same manner as the drill guide 300.

Figure 10:
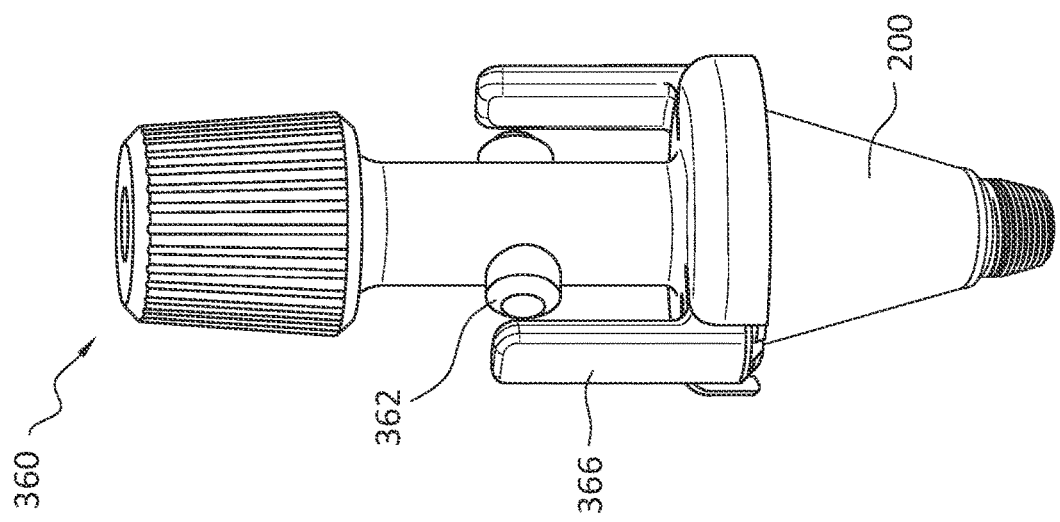
FIG. 10 illustrates another embodiment of the drill guide handle.

FIG. 10 illustrates another embodiment of the drill guide handle. The drill guide handle 360 is similar to drill guide handle 350, but adds tab stops 362. The tab stops 362 limit the range of motion of the tabs 366 as they are be pressed inward. This limits the stress on the tabs 366 to minimize the likelihood of the tabs 366 breaking. Otherwise, the guide handle 360 has the same features and operates in the same manner as the drill guide 350.

Figure 11:
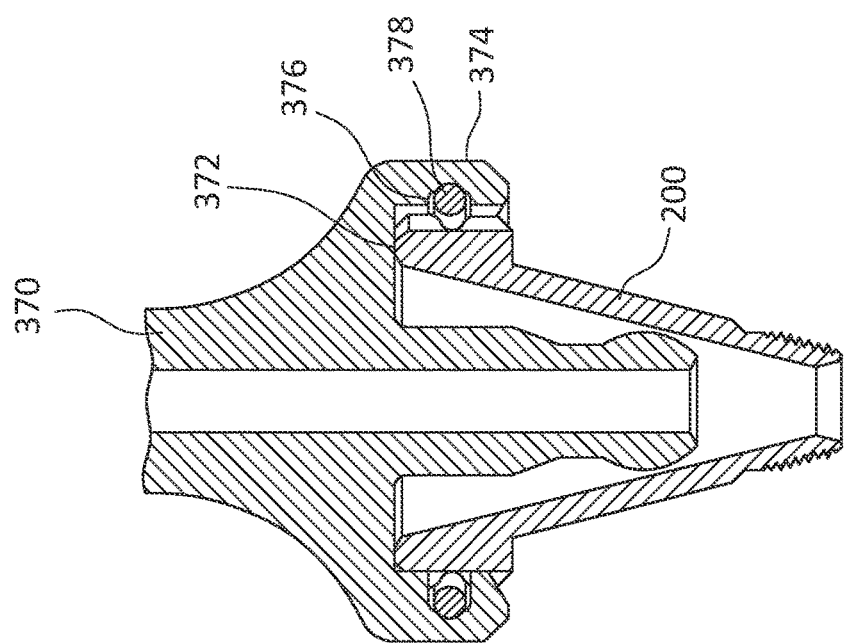
FIG. 11 illustrates another embodiment of the drill guide handle.

FIG. 11 illustrates another embodiment of the drill guide handle. The drill guide handle 370 is similar to the drill guide handle 300 except that a canted coil spring 378 is used to engage the horizontal grooves 218. The canted coil spring 378 is a donut shaped coil spring that fits in a groove 376 on the inside of the handle body 374. As the drill guide handle 300 starts to engage the drill guide 200, the canted coil spring 378 compresses to allow the drill guide handle 300 to slide over the outside of the drill guide 200. Once proximal edge 202 engages a drill guide stop surface 372, the canted coil spring 378 aligns with the horizontal grooves 212 and expands back to its normal shape to engage the horizontal grooves 212 to secure the drill guide handle 370 to the drill guide 200. Otherwise, the guide handle 370 has the same features and operates in the same manner as the drill guide 350.

Figure 12A:
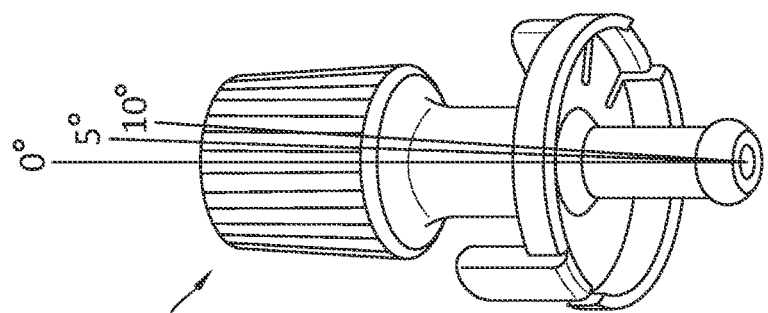
FIG. 12A illustrates another embodiment of a drill guide handle.
Figure 12B:
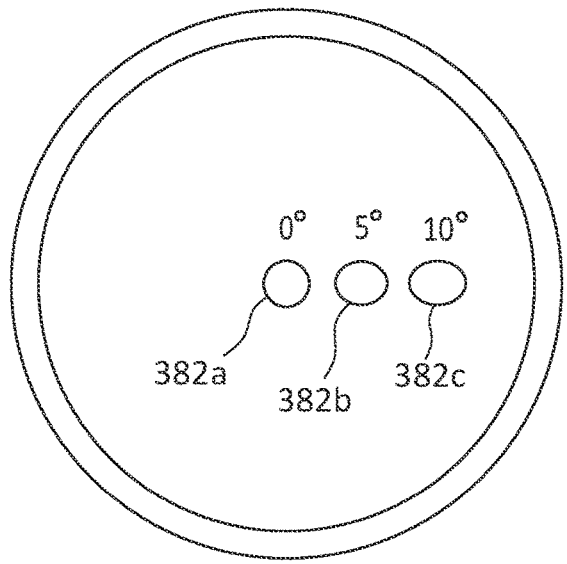
Figure 12C:
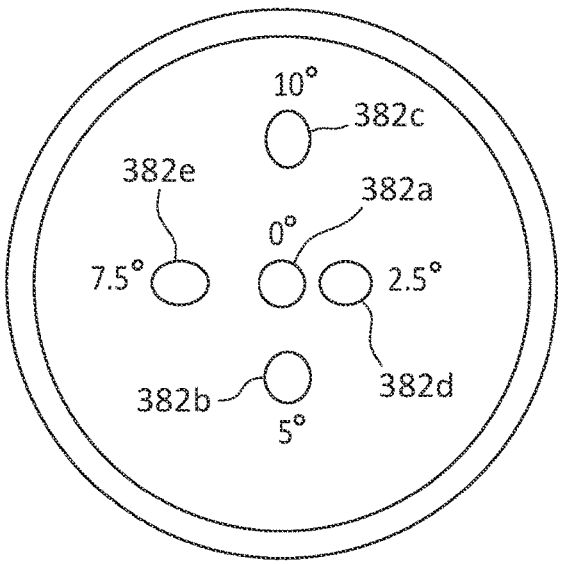

FIG. 12A illustrates another embodiment of a drill guide handle. The drill handle 380 may include a plurality of cannulas running through the drill guide handle 380 in order to allow for different fixed drilling angles. For example, in FIG. 12A, three different lines are illustrated that correspond to three different cannulas at three different insertion angles: 0°, 5°, and 10°. As a result there would be three different proximal openings 382*a-c* at the proximal end of the drill guide 380 as illustrated in FIG. 12B. FIG. 12B illustrates just the proximal end of an embodiment of the drill guide handle 380. Each proximal hole 382 may have a label indicating its associated insertion angle. Each of the cannulas would intersect at the distal opening at the distal end of the drill guide handle 380. FIG. 12C illustrates another embodiment of the distal end of the drill guide handle. In this embodiment there are five proximal holes 382*a-e* corresponding to 0°, 2.5°, 5° 7.5°, and 10° insertion angles. Each proximal hole 382*a-e* has its corresponding cannula that converges at the distal opening. In this situation the off-angle proximal holes 382*b-e* are distributed around the 0° proximal hole 382*a*. Any number of cannulas and proximal holes may be implemented in the drill guide handle to provide a variety of fixed angle drill guides to the surgeon.

FIG. 13 helps to illustrate a rotation angle. The rotation angle 402 is the angle of the screw as projected in to a tangential plane 400 of the bone. The rotation angle's axis of rotation 404 is normal to the plate hole. A zero reference angle 406 may be selected, and the rotation angle is then measured from the zero reference angle 406.

There are situations in which the surgeon wants to select a specific rotation angle for a screw inserted into a plate hole and bone. FIG. 14 illustrates that markings that may be placed on a drill guide or on a bezel of a drill guide. In various embodiments, various angle markings may be placed on the proximal edge of the drill guide or on an upper portion of the inner guide surface. The zero angle indicator 506 may be set to a specific reference direction and then the surgeon can align the drill bit to the desired rotation angle. In another embodiment, the various angle marking may be placed on a bezel. The bezel may be part of the drill guide or placed on the drill guide during use. The bezel can then be rotated to align the zero degree indicator 506 in the desired reference direction.

FIG. 15 illustrates an embodiment of a variable aperture attachment 600. The variable aperture attachment 600 may include a body 608, adjustment ring 604, and aperture leaves 606. As the adjustment ring is rotated the aperture leaves 606 move in and out to vary the size of an aperture 602. This aperture 602 provides a maximum insertion angle for the drill bit. Further, the adjustment ring 604 and the body 608 may include annotations that indicate the maximum insertion angle related to the resulting aperture as the adjustment ring is rotated. Accordingly, the surgeon may place the variable aperture attachment 600 on the drill guide and select a maximum drilling angle. Further, the variable aperture attachment 600 may securely engage the drill guide using any of the methods and structures defined above for the drill guide handles in order to prevent the variable aperture attachment 600 from rotating relative to the drill guide during adjustment.

FIG. 16 illustrates drill angle template for use with a variable angle drill guide. The drill angle template 700 may include an opening 706 at the center that receives a drill bit. The drill angle template 700 may be made of transparent material with angle markings 702 and 704. Angle markings 702 correspond to various insertion angles. Angle markings 704 correspond to various orientation angle markings as shown. FIG. 17 illustrates the drill angle template 700 placed on the proximal end of a drill guide 710. In this example the 10° insertion angle ring aligns with an inner edge 720 of the proximal end of the drill guide 710. In this position, a drill bit 712 fed through the aperture 706 will result in hole in the bone with a 10° insertion angle. Further, the hole in the bone will have an orientation angle of approximately 67.5°. FIG. 18 illustrates a drill bit 712 inserted through the drill angle template 700 and the drill guide 710. The drill bit 712 has drilled through a plate hole in the bone plate 714 into the bone 716 with a fracture 718.

The surgeon may use the drill angle template 700 by placing the drill bit 712 though the aperture 706 and the drill guide 710 so that the tip of the drill bit 712 rests on the bone to be drilled. Further, the drill angle template 700 will rest on the proximal edge of the drill guide 710. The surgeon may then rotate the drill angle template 700 to place the zero degree reference at a desired orientation. This step is optional if the orientation angle is not important. Next, the drill bit 712 is moved in the drill guide 710 until a desired insertion angle is achieved by aligning the angle indicator 702 related to the desired insertion angle with the inner edge 720. Then the surgeon begins drilling the hole.

The drill angle template 700 may be disposable. In other embodiments it may be multiple use and may be reused in multiple surgeries after proper sterilization. In another embodiment, the drill guide template may be opaque and only provides one drilling angle corresponding to the outer edge of the drill angle template 700. In this embodiment, a number of different drill angle templates may be available corresponding to different insertion angles. The surgeon then picks the drill angle template associated with the desired insertion angle. In this embodiment, the rotation angle markings may also be present. In use, the outer edge of the template is lined up with the inner edge of the inner edge of the proximal end of the drill guide.

While each of the embodiments are described above in terms of their structural arrangements, it should be appreciated that the invention also covers the associated methods of using the embodiments described above.

Although the various exemplary embodiments have been described in detail with particular reference to certain exemplary aspects thereof, it should be understood that the invention is capable of other embodiments and its details are capable of modifications in various obvious respects. As is readily apparent to those skilled in the art, variations and modifications and combinations of the various embodiments can be affected while remaining within the spirit and scope of the invention. Accordingly, the foregoing disclosure, description, and figures are for illustrative purposes only and do not in any way limit the invention, which is defined only by the claims.

What is claimed is:

1. A drill guide handle configured to engage a variable angle drill guide, comprising:
   a handle grip;
   a first cannula extending from a proximal end of the drill guide handle to a distal end of the drill guide handle, wherein the first cannula is configured to provide a single zero degree insertion angle for a drill bit; and
   a body comprising:
      a first tab and a second tab wherein the first and second tabs include a first and second tab protrusion, respectively, wherein each of the first tab and the second tab is configured to flex so that the first and second tab protrusions engage a horizontal groove on the variable angle drill guide;
      a body protrusion on an inner surface of the body, wherein the body protrusion is configured to engage a vertical groove on the variable angle drill guide;
      a body edge at an end of the body distal to the first and second tabs, wherein the body edge is continuous in a single plane;
      a first tab border opening configured to form the first tab, wherein an outer surface of the first tab substantially conforms to a shape of an outer surface of the body; and
      a second tab border opening configured to form the second tab, wherein an outer surface of the second tab substantially conforms to a shape of the outer surface of the body.

2. The drill guide handle of claim 1, wherein the first tab and the second tab extend substantially along a direction of an axis of the first cannula from the proximal end to the distal end of the drill guide handle.

3. The drill guide handle of claim 1, wherein the first tab and the second tab extend in a direction substantially perpendicular to an axis of the first cannula.

4. The drill guide handle of claim 1, wherein the first cannula includes a proximal cannula portion and a distal cannula portion, wherein a cross-sectional size of the proximal cannula portion is larger than a cross-sectional size of the distal cannula portion.

5. The drill guide handle of claim 4, wherein the proximal cannula portion is configured to accept a driver.

6. The drill guide handle of claim 5, wherein the first cannula further comprises a middle cannula portion with a cross-sectional shape complementary to an end of the driver, wherein the middle cannula portion is configured to grip the end of the driver.

7. The drill guide handle of claim 4, wherein a cross-sectional area of the distal cannula portion is configured to accommodate the drill bit passing therethrough.

8. The drill guide handle of claim 1, wherein the body edge has a chamfer on an inner side.

9. The drill guide handle of claim 8, further comprising a drill guide stop inside the body configured to stop the variable angle drill guide when engaged with the drill guide handle and configured to align the first and second tab protrusions with the horizontal groove.

10. The drill guide handle of claim 1, wherein the variable angle drill guide comprises:
    a frustoconical body with a first opening at a narrower distal end of the frustoconical body and a second opening at a wider proximal end of the frustoconical body; and
    a grip surrounding the wider proximal end of the frustoconical body, where the grip includes the horizontal groove and the vertical groove.

11. The drill guide handle of claim 10, wherein the narrower distal end of the frustoconical body includes threads on an outer surface of the narrower distal end of the frustoconical body, wherein the threads are configured to engage threads in a plate hole of a bone plate.

12. A method of inserting a variable angle drill guide into a bone using the drill guide handle of claim 11, comprising:
    connecting the drill guide handle to the variable angle drill guide by sliding the drill guide handle over the grip of the variable angle drill guide until the first and second tab protrusions engage the horizontal groove and where the sliding the drill guide handle over the grip further includes aligning the body protrusion with the vertical groove on the grip;
    screwing the threads of the variable angle drill guide into the plate hole of the bone plate;
    drilling a hole in the bone by placing the drill bit in the first cannula, wherein the drilled hole is a zero degree insertion angle hole; and
    unscrewing the threads of the variable angle drill guide from the plate hole of the bone plate.

13. The method of claim 12, further comprising:
    inserting a driver into the first cannula of the drill guide handle prior to the screwing the threads of the variable angle drill guide into the plate hole of the bone plate, wherein the screwing the threads of the variable angle drill guide into the plate hole of the bone plate includes rotating the driver, and
    the unscrewing the threads of the variable angle drill guide from the plate hole of the bone plate includes rotating the driver.

14. A method of inserting a variable angle drill guide into a bone using the drill guide handle of claim 11, comprising:
    connecting the drill guide handle to the variable angle drill guide by sliding the drill guide handle over the grip of the variable angle drill guide until the first and second tab protrusions engage the horizontal groove and where the sliding the drill guide handle over the grip further includes aligning the body protrusion with the vertical groove on the grip;

screwing the threads of the variable angle drill guide into the plate hole of the bone plate;

removing the drill guide handle from the variable angle drill guide;

drilling a hole in the bone by placing the drill bit in the variable angle drill guide, wherein the drilled hole has an insertion angle other than zero degrees;

reconnecting the drill guide handle to the variable angle drill guide; and unscrewing the threads of the variable angle drill guide from the plate hole of the bone plate.

15. The method of claim 14, further comprising:

inserting a driver into the first cannula of the drill guide handle prior to the screwing the threads of the variable angle drill guide into the plate hole of the bone plate, wherein the screwing the threads of the variable angle drill guide into the plate hole of the bone plate includes rotating the driver, and the unscrewing the threads of the variable angle drill guide from the plate hole of the bone plate includes rotating the driver.

16. A drill guide system, comprising:

a variable angle drill guide comprising:

a frustoconical body with a first opening at a narrower distal end of the frustoconical body and a second opening at a wider proximal end of the frustoconical body; and a grip surrounding the wider proximal end of the frustoconical body, where the grip includes a horizontal groove and a vertical groove, a drill guide handle comprising:

a handle grip;

a first cannula extending from a proximal end of the drill guide handle to a distal end of the drill guide handle, wherein the first cannula is configured to provide a single zero degree insertion angle for a drill bit; and a body comprising:

a first tab and a second tab wherein the first and second tabs include a first and second tab protrusion, respectively, wherein each of the first tab and the second tab is configured to flex so that the first and second tab protrusions engage the horizontal groove on the variable angle drill guide; and a body protrusion on an inner surface of the body, wherein the body protrusion is configured to engage the vertical groove on the variable angle drill guide.

* * * * *